United States Patent
Damadian et al.

(10) Patent No.: US 6,507,192 B1
(45) Date of Patent: Jan. 14, 2003

(54) NUCLEAR MAGNETIC RESONANCE APPARATUS AND METHODS OF USE AND FACILITIES FOR INCORPORATING THE SAME

(75) Inventors: Raymond V. Damadian, Woodbury, NY (US); Gordon T. Danby, Wading River, NY (US); John W. Jackson, Shoreham, NY (US); Hank Hsieh, Berkeley, CA (US); Terry Morrone, Greenlawn, NY (US); Timothy Damadian, Huntington Station, NY (US)

(73) Assignee: Fonar Corporation, Melville, NY (US)

( * ) Notice: Subject to any disclaimer, the term of this patent is extended or adjusted under 35 U.S.C. 154(b) by 0 days.

(21) Appl. No.: 10/011,327

(22) Filed: Oct. 22, 2001

Related U.S. Application Data

(60) Division of application No. 09/295,532, filed on Apr. 21, 1999, now Pat. No. 6,373,251, which is a division of application No. 07/993,072, filed on Dec. 18, 1992, now Pat. No. 6,023,165, which is a continuation-in-part of application No. 07/952,810, filed on Sep. 28, 1992, now Pat. No. 5,754,085.

(51) Int. Cl.[7] ................................................. G01V 3/00
(52) U.S. Cl. ........................................................ 324/318
(58) Field of Search ................................ 324/319, 320, 324/318, 300, 306, 307, 309; 600/410; 335/216, 296

(56) References Cited

U.S. PATENT DOCUMENTS

| | | |
|---|---|---|
| 4,534,358 A | 8/1985 | Young |
| 4,608,991 A | 9/1986 | Rollwitz |
| 4,613,820 A | 9/1986 | Edelstein et al. |
| 4,651,099 A | 3/1987 | Vinegar et al. |
| 4,668,915 A | 5/1987 | Daubin et al. |
| 4,707,663 A | 11/1987 | Minkoff et al. |
| 4,766,378 A | 8/1988 | Danby et al. |
| 4,777,464 A | 10/1988 | Takabatashi et al. |
| 4,829,252 A | 5/1989 | Kaufman |
| 4,875,485 A | 10/1989 | Matsutani |
| 4,968,937 A | 11/1990 | Akgun |
| 4,985,678 A | 1/1991 | Gangarosa |

(List continued on next page.)

FOREIGN PATENT DOCUMENTS

| | | |
|---|---|---|
| GB | 3140-225 | 10/1981 |
| JP | 4-332531 | 11/1992 |
| JP | 62-26052 | 8/1994 |

OTHER PUBLICATIONS

Weis et al., Simulation of the Influence of Magnetic Field Inhomogeneity and Distortion Correction in MR Imaging, 8(4):483–89 (1990) (Abstract).

Primary Examiner—Louis Arana
(74) Attorney, Agent, or Firm—Lerner, David, Littenberg, Krumholz & Mentlik, LLP

(57) ABSTRACT

NMR apparatus for achieving construction of improved patient access. Facilities and methods of mobile and fixed site scanning.

4 Claims, 20 Drawing Sheets

U.S. PATENT DOCUMENTS

| | | |
|---|---|---|
| 5,008,624 A | 4/1991 | Yoshida |
| 5,061,897 A | 10/1991 | Danby et al. |
| 5,124,651 A | 6/1992 | Dandy et al. |
| 5,153,546 A | 10/1992 | Laskaris |
| 5,194,810 A | 3/1993 | Breneman et al. |
| 5,207,224 A | 5/1993 | Dickinson et al. |
| 5,229,723 A | 7/1993 | Sakurai et al. |
| 5,250,901 A | 10/1993 | Kaufman et al. |
| 5,291,890 A | 3/1994 | Cline et al. |
| 5,305,749 A | 4/1994 | Li et al. |
| 5,315,276 A | 5/1994 | Huson et al. |
| 5,382,904 A | 1/1995 | Pissanetsky |
| 5,412,363 A | 5/1995 | Breneman et al. |
| 5,436,607 A | 7/1995 | Chari et al. |
| 5,490,513 A | 2/1996 | Damadian et al. |
| 5,519,372 A | 5/1996 | Palkovich et al. |
| 5,592,090 A | 1/1997 | Pissanetzky ................. 324/319 |
| 5,606,970 A | 3/1997 | Damadian |
| 5,623,241 A | 4/1997 | Minkoff ...................... 335/296 |
| 5,666,056 A | 9/1997 | Cuppen ...................... 324/318 |
| 6,373,251 B1 * | 4/2002 | Damadian et al. .......... 324/318 |

* cited by examiner

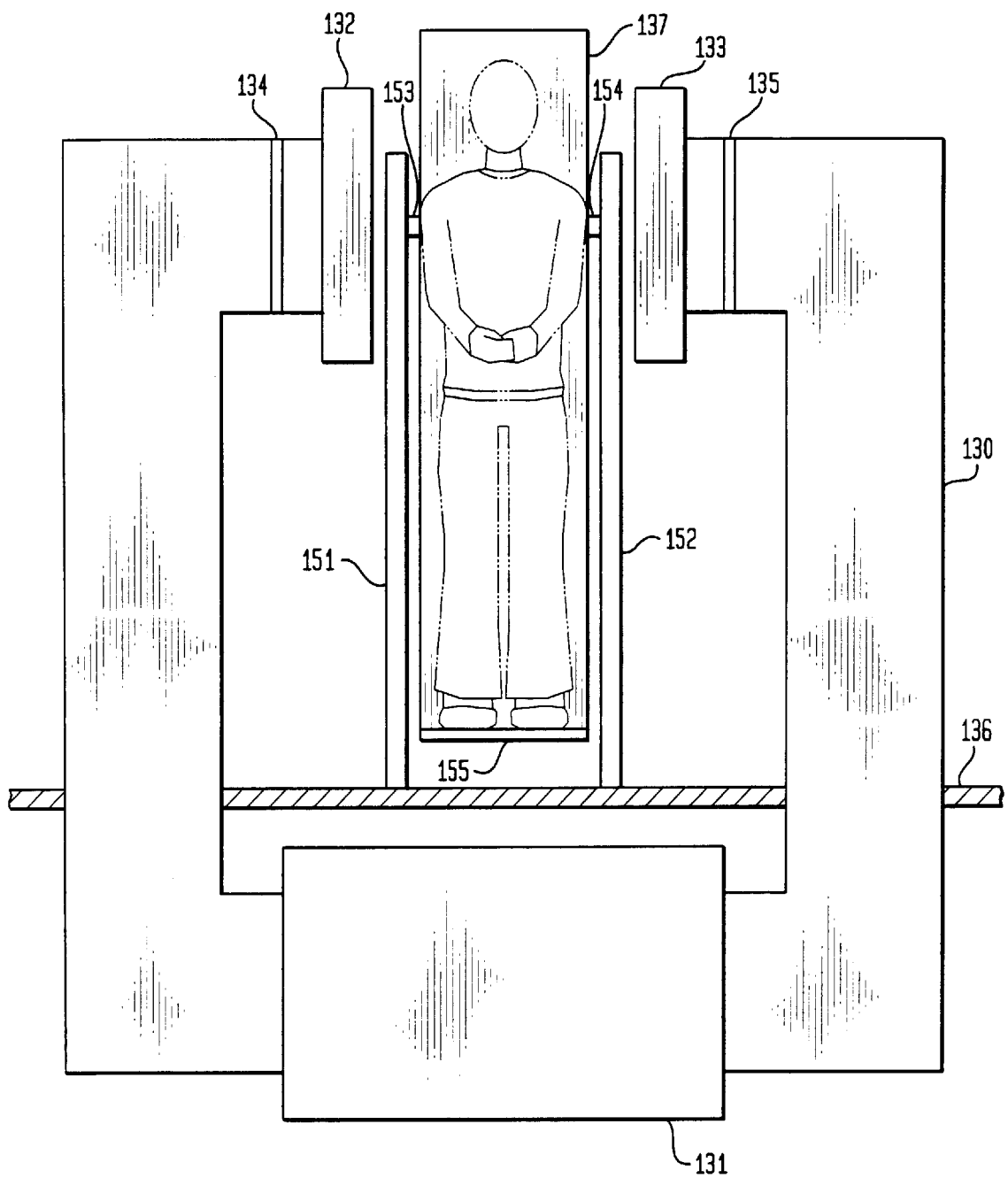

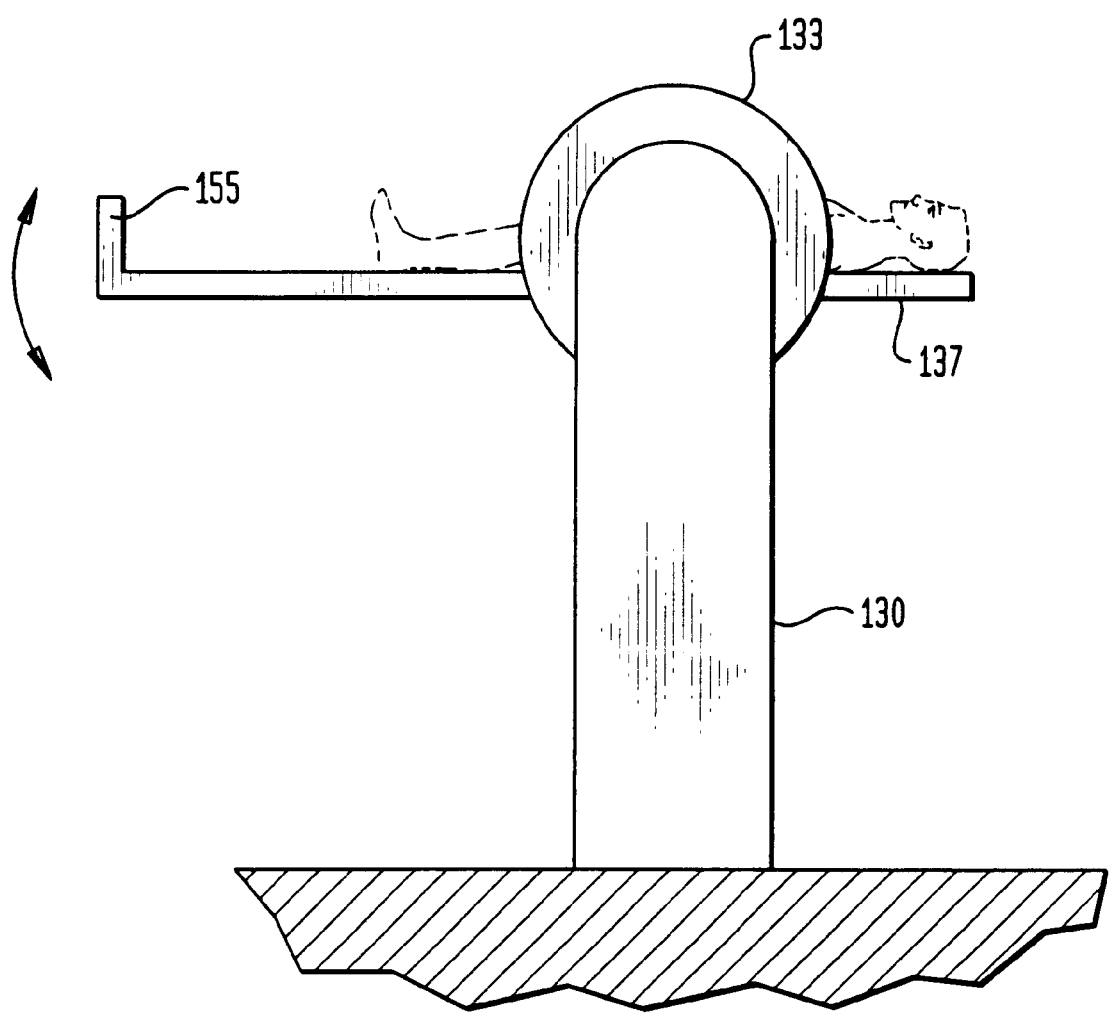

NUCLEAR MAGNETIC RESONANCE APPARATUS AND METHODS OF USE AND FACILITIES FOR INCORPORATING THE SAME

CROSS-REFERENCE TO RELATED APPLICATION

The present application is a divisional application of application Ser. No. 09/295,532 filed on Apr. 21, 1999, now U.S. Pat. No. 6,373,251 which is a divisional of application Ser. No. 07/993,072 filed on Dec. 18, 1992, now U.S. Pat. No. 6,023,165 which is a Continuation-in-Part of application Ser. No. 07/952,810 filed on Sep. 28, 1992 which has issued into U.S. Pat. No. 5,754,085 of Raymond V. Damadian, Gordon T. Danby, John W. Jackson, Hank Hsieh, Terry Morrone and Timothy Damadian and entitled Nuclear Magnetic Resonance Apparatus and Methods of Use and Facilities for Incorporating the Same, the disclosures of which are hereby incorporated herein.

BACKGROUND OF THE INVENTION

The present invention relates to magnets for medical magnetic resonance studies and more particularly to such magnets which comprise a ferromagnetic yoke as part of the magnet structure.

Medical magnetic resonance (MR) studies are typically carried out in strong magnetic fields greater than one kilogauss. In addition to a strong magnetic field, medical magnetic resonance studies typically require a magnetic field homogeneity of the order of a few parts per million. Considerable effort has been invested in improving magnets for medical MR with a goal toward achieving the field strengths required while attaining the necessary field homogeneity over a sufficiently large spatial volume in a structure that is clinically acceptable and commercially feasible.

One technique for improving magnet efficiency is to incorporate within the magnet structure a ferromagnetic yoke which not only comprises part of the structural support but which also defines a magnetic flux return path. The use of ferromagnetic return paths in medical magnetic resonance scanner magnets is disclosed in U.S. Pat. No. 4,675,609 to Danby et al. Ferromagnetic yoke structure is likewise disclosed in U.S. Pat. No. 4,672,346 to Miyamoto et al. In addition to improving efficiency, the incorporation of a ferromagnetic flux return path can also be used to eliminate strong leakage magnetic fields which are inherent in aircore solenoidal magnets.

It would be desirable to incorporate ferromagnetic yokes in medical MR magnets having a strong magnetic field. The stronger the magnetic field developed by the magnet, however, the more difficult it is to achieve a magnet structure which would be considered practical by the medical community for clinical use.

To avoid magnetic saturation of the ferromagnetic yoke at high field strengths, the dimensions of the yoke cross sections along the flux return path become substantial. Greater yoke cross-sectional area results, of course, in an increase in magnet weight.

Additionally, larger yoke structures can result in obstructions which hinder easy access to and egress from the patient gap of the magnet where a patient is situated during magnetic resonance scanning. Any compromises to the required yoke design from the standpoint of flux return path reluctance, in order to accommodate patient access, can materially increase the magnetic leakage field and reduce the homogeneity of the magnetic field within the gap. Another desirable feature in a medical MR magnet is a large gap for receiving the patient to be studied. A large gap facilitates patient positioning and permits large patients to be studied by magnetic resonance. A related but distinct consideration which is impacted by gap size is that of access to a patient by medical personnel while the patient is within the gap.

Yet another desired improvement to medical MR magnets is the provision of features or means to suppress the generation of eddy currents, particularly within the poles of the magnet. Most medical MR scanning techniques in use at this time involve the use of time-varying magnetic fields, usually in the form of pulsed magnetic field gradients. These time-varying magnetic fields may induce eddy currents in conductive parts of the magnet, and such eddy currents will in turn generate magnetic fields which can degrade magnetic field stability during data acquisition and field homogeneity of the magnet. Suppression of eddy currents is therefore highly desirable.

Accordingly, it is an object of the invention to provide a magnet having a ferromagnetic yoke with a strong field for use in medical magnetic resonance studies which has a large gap and a structure providing open entry to the gap. Moreover magnets currently employed today to generate high field MRI most generally employ air-core superconductors and do not utilize ferromagnetic structures to concentrate field in the imaging region. Such air-core magnets that fail to exploit the benefits of ferromagnetic flux concentration are fundamentally inefficient as compared to ferromagnetic core magnets and require as much as eight times as many ampere-turns to achieve the same center field as a ferromagnetic core (e.g. iron core) electromagnet (e.g. iron core superconducting magnet) as covered by U.S. Pat. No. 4,766,378, for Nuclear Magnetic Resonance Scanners and commonly assigned herewith.

It is another object of the invention to provide a magnet having a ferromagnetic yoke for medical magnetic resonance scanning and having a large patient gap, and selected dimensions, geometry and materials in order to improve the magnet.

It is another object of the invention to provide a magnet for medical magnetic resonance studies which has a ferromagnetic yoke with a structure that provides open entry to the patient gap of the magnet, together with structure for eddy current suppression.

It is another object of the invention to provide a magnet and MR apparatus that would be suitable to function in a surgical operating room environment to provide images for MRI guided surgery.

SUMMARY OF THE INVENTION

According to the invention a magnet for use in medical magnetic resonance studies develops a magnetic field within its gap. A pair of opposed ferromagnetic poles face each other and define a patient-receiving gap between them for receiving the body of a patient to be studied by magnetic resonance. A ferromagnetic yoke supports the poles in position facing each other, and is configured to provide open entry to the patient gap.

In a preferred embodiment the ferromagnetic yoke is comprised of upper and lower pole supports each for supporting a respective one of the poles, and at least three ferromagnetic columns for supporting the upper pole support above the lower pole support. The upper and lower pole supports and the columns together establish a magnetic flux return path for magnetic flux which passes from one pole to the other through the patient gap.

Means for generating magnetic flux generates a magnetic flux flowing from one to the other of the poles across the gap and through the yoke back to the one of the poles. In various preferred embodiments the means for generating magnetic flux is comprised of permanent magnet material, a superconductive magnet or a resistive electromagnet.

BRIEF DESCRIPTION OF THE DRAWING

Additional objects and features of the invention will appear from the following description of the preferred embodiments of the invention in conjunction with the accompanying drawing in which:

FIGS. 12 and 13 are front and side elevations, respectively, of a device for scanning patients in different orientations and which incorporates the magnet according to the invention;

DETAILED DESCRIPTION OF THE PREFERRED EMBODIMENTS

Magnetic Resonance Magnets

The magnets according to the invention are constructed for carrying out whole body scanning. As such, the patient-receiving gap of the magnet is sufficiently large to accommodate enough of the patient's torso to permit imaging of any desired region of the torso, and the magnet yoke and pole surfaces permit patient entry into the gap and develop a sufficiently large region of magnetic field to allow acquisition of torso images.

Figure 1:
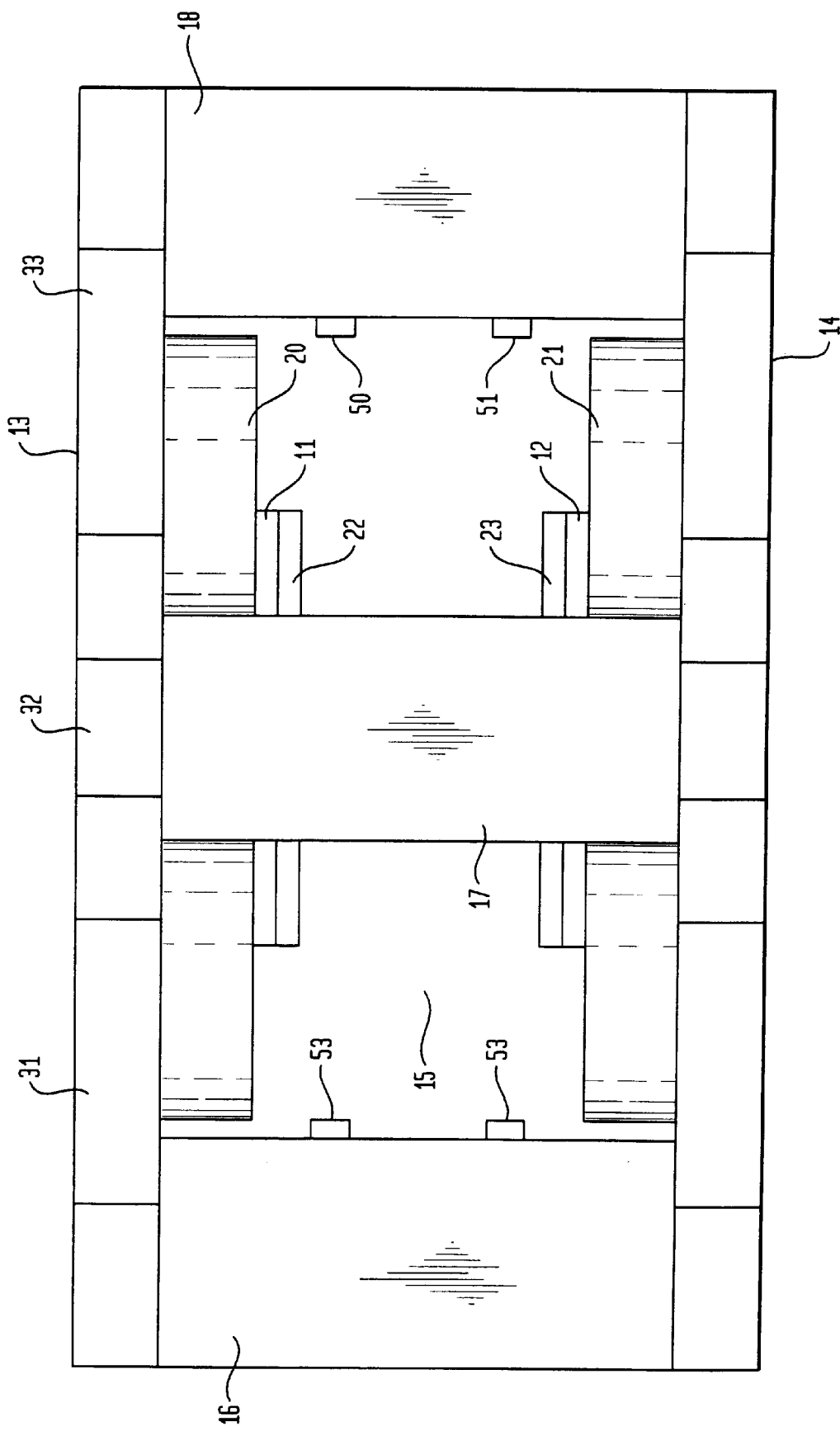
FIG. 1 is a front elevation of the magnet according to the invention.

The magnet according to the present invention, shown in FIG. 1, is comprised of a pair of ferromagnetic poles 11 and 12 respectively mounted on an upper pole support 13 and a lower pole support 14. A patient-receiving gap 15 between the poles 11 and 12 is sufficiently large to receive the body of a patient who is to undergo study by magnetic resonance. The upper and lower pole supports 13, 14 are supported by a plurality of columns. The illustrated embodiment has four columns, 16–19, three of which are visible in the view shown. Means 20 and 21 develops magnetic flux which passes through the gap 15 between the poles 11 and 12. A pair of annular ferromagnetic structures 22, 23 called shim bars are disposed on the pole surfaces or faces of poles 11, 12, respectively. The shim bars are used to reduce fringing of the magnetic field around the periphery of the poles 11, 12, thereby increasing the volume of uniform magnetic field.

Figure 2:
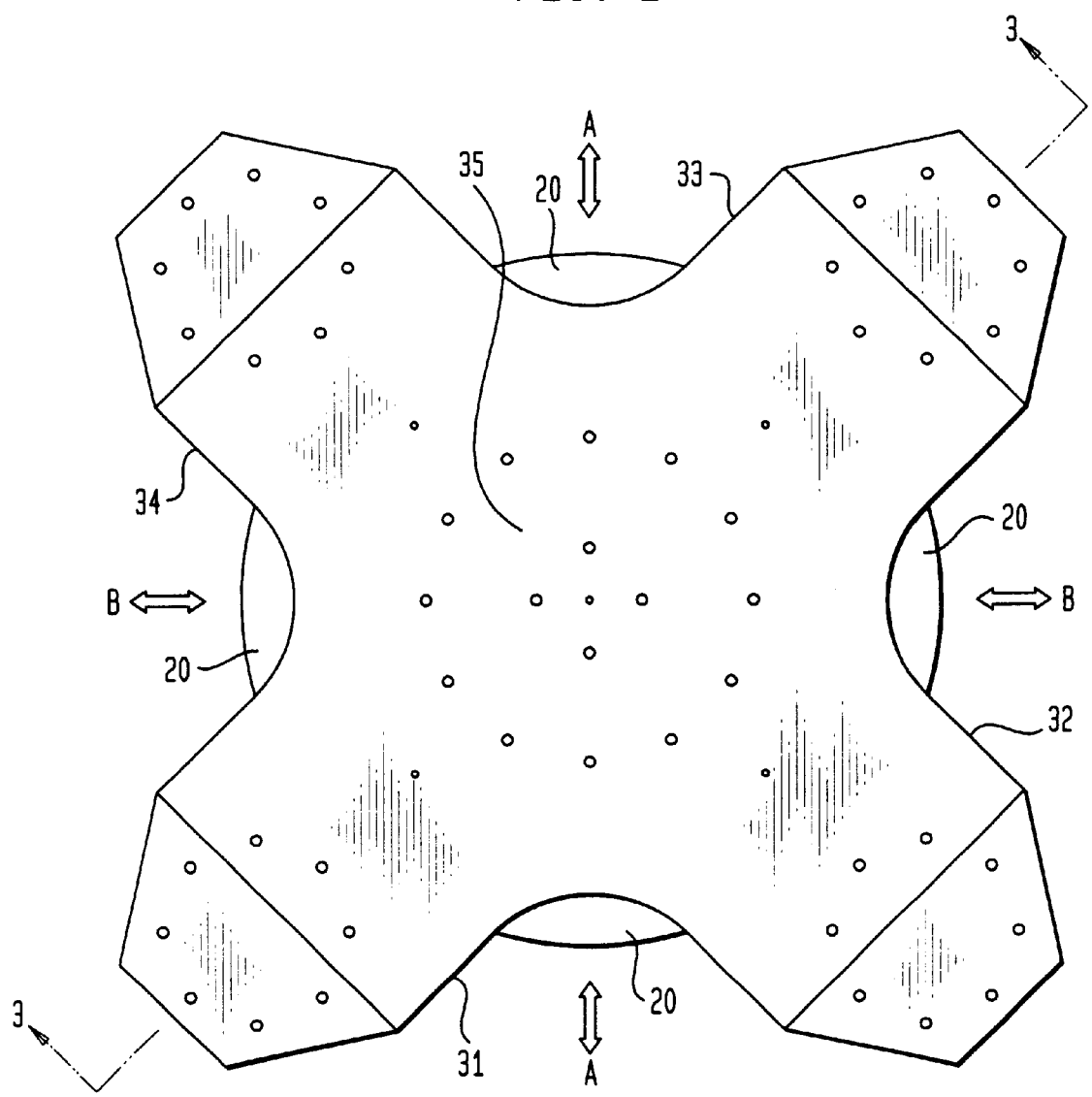
FIG. 2 is a plan view of the magnet according to the invention.

FIG. 2 is a plan view of the magnet according to the present invention. The pole support 13 has four legs 31–34 extending from a central region 35 of the support. The columns 16–19 (FIG. 1) together support the pole support 13, each at a respective one of the legs 31–34. The spaces between adjacent legs provide access to the patient-receiving gap of the magnet.

An important aspect of the present invention is that the structure of the magnet yoke defines two different non-collinear directions of access for either medical personnel or a patient to gain access to the patient-receiving gap 15. As used herein "collinear" means lying along the same or parallel directions, and non-collinear means directions that are not parallel and therefore intersect at some point in space. Non-collinearity will be satisfied by any directions when the angle between the directions causes an intersection of these directions at some point in space. Accordingly, the non-collinear directions can have any non-zero angle between them.

Figure 3:
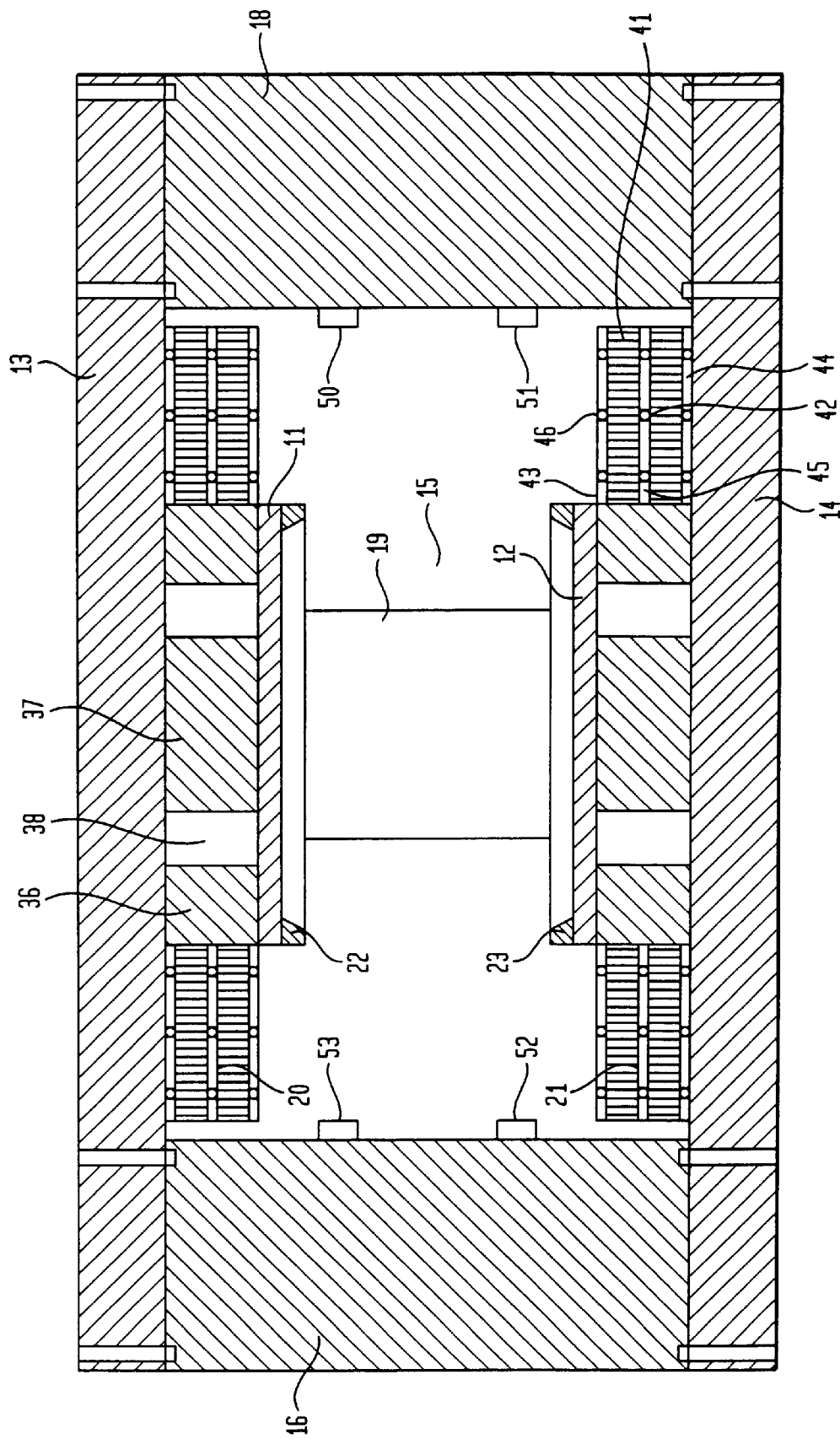
FIG. 3 is a vertical section of the magnet according to the invention taken along the section line 3—3 in FIG. 2.

As shown in FIGS. 1–3, column 16 supports leg 31, column 17 supports leg 32, column 18 supports leg 33 and column 19 supports leg 34. One access direction identified by the double-headed arrows "A" in FIG. 2 extends along a line through the gap between the pair of legs 31, 32 and corresponding columns 16, 17 and between the pair of legs 33, 34 and the corresponding columns 18, 19. Another access direction identified by the double-headed arrows "B" in FIG. 2 extends along a line through the gap between the pair of legs 32, 33 and corresponding columns 17, 18 and between the pair of legs 31, 34 and corresponding columns 16, 19. The directions A and B are non-collinear, and not necessarily perpendicular, and allow patient entry into the gap 15 along either of them. Once the patient is in the gap attending medical personnel can gain access to the patient along either direction, and along both directions simultaneously.

As used herein, "open entry" refers to the structural feature of the magnet yoke which allows patient entry into (or egress from) the gap, and access to the patient while in the gap, along two or more non-collinear directions up to and including 360 degrees of different directions, and the absence of obstructions which would destroy the open entry feature. This open entry feature has not been available in practice in magnets for medical magnetic resonance having ferromagnetic yokes, except in low field strength systems of around 600 gauss. Prior systems of greater field strength either have a yoke which defines a single access direction or the yoke is housed within a covering shell that obstructs all but a single direction for gap access.

FIG. 3 is a vertical section taken along the line 3—3 in FIG. 2. The upper and lower supports 13, 14 are secured to the columns, for example, by threaded shafts. The poles 11 and 12 are secured to the pole supports 13 and 14 through the intermediary of pole stems. In the preferred embodiment shown, each pole stem is comprised of two elements; an annular outer piece and a central core. Thus, the pole 11 is secured to the pole support 13 through the pole stem comprised of the annular body 36 and the cylindrical core 37. An annular air gap 38 is defined between the elements 36 and 37 of the pole stem, and the air gap 38 extends from the pole support 13 to the pole 11. The pole 12 is similarly secured to the pole support 14 through the intermediary of a lower pole stem comprised of an identical annular element and cylindrical core having an annular air gap between them.

Magnetic flux developed by the coil 20 flows through the pole stem elements 36 and 37 and into the pole 11. The magnetic flux leaves the pole 11 and crosses the gap 15 to enter the pole 12. The flux then travels through the lower pole stem into the pole support 14, divides and returns through the columns 16–19 and the pole support 13. The magnetic flux developed by the coil 21 follows the same path as the flux developed by the coil 20.

The two-piece construction of the pole stems with the annular air gap between the pole stem elements saves weight while at the same time improving magnetic field uniformity across the pole surface or pole face. Most of the magnetic flux delivered to the pole 11, for example, will flow through the pole stem elements 36 and 37 with a negligible amount of flux flowing through the air gap 38. Flux delivered to the pole 11 through the pole stem elements 36 and 37 distributes itself within the pole 11 so as to be sufficiently uniform to carry out the magnetic resonance studies intended. Additionally, shim bars comprised of annular ferromagnetic members 22, 23 are each disposed on the pole surface of a respective one of the poles 11, 12. The shim bars 22, 23 are approximately the pole diameter and typically have a beveled inner surface facing the pole center. The shim bars improve the uniformity within the gap 15 by minimizing flux leakage.

The coils 20, 21 have identical structures so that only the structure of coil 21 will be described in detail. The coil 21 is comprised of stacked layers 41, 42 of conductor turns which define an electromagnet. The conductor turns are preferably aluminum or copper insulated by a fiberglass tape. A pair of external cooling plates 43, 44 one above and one below, are in thermal contact with the layers 41, 42 of conductor turns for cooling them. A third cooling plate 45 is between the layers 41, 42 of conductor turns and in thermal contact with them. All three of the cooling plates are preferably aluminum.

In the preferred embodiment the cooling plates include internal conduits which provide flow paths for cooling fluid to flow through them and carry away heat generated by current flowing through the layers of conductor turns. For example, the upper cooling plate 43 includes conduit 46 which traverses the plate in some pattern, for example, a spiral. Heat generated by resistive heating of the conductor comprising the layer 41 flows into the cooling plate 43 and then into cooling fluid within the conduit 46. By circulating the cooling fluid through a heat exchanger, an equilibrium condition can be achieved at a temperature lower than that which would occur if the conductor layers 41, 42 were cooled by natural convection and radiation only.

An alternative to the use of cooling plates is to use for the layers of conductor turns a thick conductor which has a continuous internal conduit along its length to circulate cooling fluid within the conductor. This allows fluid cooling to be achieved without having to provide any additional heat transfer structure such as the cooling plates described.

Additionally, a superconducting electromagnet, can be used in place of the disclosed resistive electromagnet.

This type of magnet can have the same annular structure surrounding the pole stem as the illustrated resistive electromagnet, or a single or a plurality of super conducting electromagnets can be positioned on another part of the magnet yoke as shown in subsequently described embodiments. Alternatively, permanent magnet material, preferably concentrated under the poles, can be used as the flux generating means.

Optionally, auxiliary magnets can be provided to help offset leakage of the magnetic field at the edges of the magnet poles 11, 12. FIGS. 1 and 3 show a pair of auxiliary magnets 50, 51 mounted on column 18, and a pair of auxiliary magnets 52, 53 mounted on column 16. Similar magnets (not shown) are mounted on columns 17 and 19. The auxiliary magnets are positioned and oriented so that their respective magnetic fields are oriented radially relative to the poles 11, 12 and so that their respective magnetic fields tend to cancel leakage fields extending beyond the edges of the poles 11, 12. These auxiliary magnets consequently improve the magnetic field homogeneity within the gap 15.

An additional feature of the magnet according to the invention is the incorporation of structure for suppressing eddy currents which may be generated, particularly within the magnet poles, during MR studies carried out with the present magnet. These eddy currents are generated by time-varying magnetic fields developed during the course of an MR study carried out with the magnet.

Figure 4A:
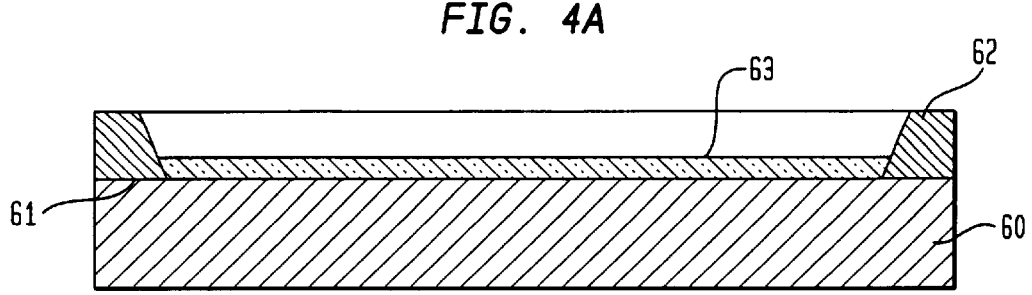
FIGS. 4A–4C are vertical sections of magnet poles having eddy current suppressing structure.

FIG. 4A is a vertical section of a pole 60 with a face or pole surface 61. A shim bar 62 is mounted on the pole surface 61. In order to suppress eddy currents, a layer 63 of eddy current-suppressing material is disposed on the pole surface 61. The material of layer 63 has a sufficiently high magnetic permeability to suppress eddy currents relative to eddy currents which would be developed within the pole in the absence of the material layer 63. The material layer 63 covers at least a principal portion of the pole surface 61. Any eddy currents generated during an MR study will occur in the material layer 63, and not in the underlying pole 60, and consequently will be weaker and shorter lived than if the material layer had not been present. Materials suitable for the layer 63 are disclosed in U.S. Pat. No. 5,061,897 to Danby, et al., commonly assigned herewith, and incorporated herein by reference.

Figure 4B:
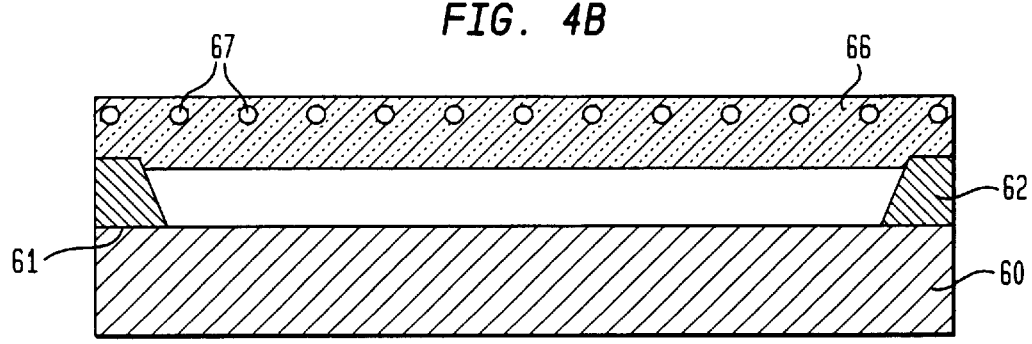

Another structure for suppressing eddy currents is shown in FIG. 4B. An insulative support 66 is disposed opposite the pole surface 61 of the pole 60. The support 66 provides a support for conductors 67 which conduct electrical current to develop gradient magnetic fields during the course of MR studies carried out with the magnet. The support 66 positions the conductors away from the pole surface 61 in order to increase the distance between the pole surface and the conductors and reduce the strength of induced eddy currents in the pole. Within a range of about one to six inches, eddy current generated fields increase approximately linearly with decreasing distance between the conductors 67 and the pole surface 61. Thus, the positioning of the conductors 67 by the support 66 spaced from the pole surface 61 is effective to suppress eddy currents in the pole 60.

Figure 4C:
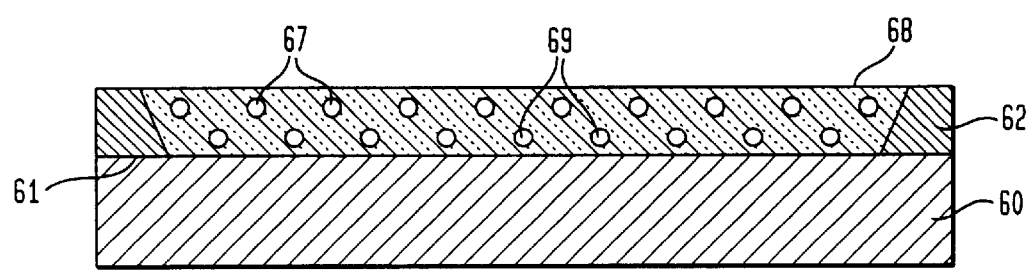

Eddy currents can also be suppressed by shielding the gradient magnetic fields from the magnet pole. FIG. 4C is a vertical section showing the use of self-shielded gradient producing conductors for achieving eddy current suppression. An insulative support 68 is disposed on the pole surface 61 of the pole 60. The support 68 provides a support for the conductors 67 which are used for developing gradient magnetic fields in the manner previously described. A layer of second conductors 69 is supported by the support 68 at a position between the conductors 67 and the pole surface 61. The second conductors 69 are electrically in series with the conductors 67 so that the same current flows through both of them. The second conductors 69 are disposed to develop a magnetic field which at least partially cancels the magnetic field developed by the conductors 67, in the region of space on the side of the layer of conductors 69 which is opposite the conductors 67, where the pole 60 is situated.

The cancellation of the magnetic field in the region of the pole 60 will effectively suppress eddy currents generated by time-varying magnetic fields developed by current flowing through the conductors 67. The use of self-shielded gradient conductors is more fully described in pending U.S. patent application Ser. No. 07/917,223 filed Jul. 23, 1992, of Terry Morrone for Optimized Gradient Coils and Shim Coils For Magnetic Resonance Scanning Systems, which is commonly assigned herewith.

The use of self-shielded gradient generating conductors has an advantage that the conductors 67 can be close to the pole surface 61 and not protrude into the magnetic gap. This allows maximum gap size while at the same time allowing for eddy current suppression. Typically, 3000 gauss magnets intended for medical MR studies have had a twenty inch gap dimension, as measured from pole surface to pole surface. Accordingly, it has been considered desirable to position the gradient generating conductors 67 and the associated support 68 no higher than the tops of the shim bars 62 in order to maximize the space available for a patient.

An important feature of the present invention is that it expands the magnet gap dimension to twenty-two inches or greater. Larger gap dimensions improve the ability to scan large patients and improve access to the patient while within the magnet gap. At the same time, the larger gap dimension of the invention renders the structure of FIG. 4B practicable. With the larger gap dimension it is possible to position the gradient generating conductors further from the pole surface while still achieving increased patient clearance and patient access. Placing the gradient generating conductors above the shim bar has the added advantage of freeing them from the dimensional constraints of the shim bar inner diameter. This allows the gradient generating conductors to span a greater transverse dimension than if they were to be within the inner diameter of the shim bar. The greater transverse dimension of the gradient generating conductors will result in improved gradient magnetic field linearity. For example, the embodiment of FIG. 4B has a layer of gradient generating conductors 67 which spans the entire width of the pole 60.

Another important feature of the invention is the range of magnetic field strengths of the particular embodiments of the invention. Heretofore, open access magnets for medical magnetic resonance imaging (MRI) have been made with a field strength of around 600 gauss and a four post design. Four post MRI magnets in the 2000 to 3000 gauss range have all been made with external magnet housings that limit gap access to a single direction through a single bore in the magnet housing. In addition, four post ferromagnetic yoke magnets have been limited to magnets with a field strength of 3000 gauss or less, and ferromagnetic yoke magnets of any design have been limited to 4000 gauss or less. Open access magnets with ferromagnetic yokes at greater field strengths, and such magnets with expanded gap dimensions and improved gap access, as disclosed herein, constitute substantial advances over the more limited designs employed heretofore.

The ferromagnetic material used in the magnets according to the invention is preferably a low silicon steel which exhibits a sufficiently high magnetic permeability to permit the magnet to achieve the magnetic field strength at which it is intended to operate.

As magnet field strength increases, pole and shim bar saturation may place practical limits on the magnet design and can introduce practical constraints on the size of the magnet poles, magnetic field strength and gap distance. Accordingly, it is desirable that every means be taken to reduce the tendency toward magnetic saturation.

Heretofore, the applicants have fabricated 3,000 gauss magnets using grade 1008 steel. This material is a low silicon-content steel having a carbon content of less than 0.08 atomic percent. It is satisfactory for the ferromagnetic material in conventional medical MR magnets which have field strengths in the 600–3000 gauss range.

The applicants have discovered that steel with a somewhat lower carbon content than that previously used enables the realization of substantially higher field strengths than in prior medical MR magnets. In particular, magnetic field strengths in excess of 5,000 gauss can be readily achieved, and field strengths greater than 10,000 gauss are feasible. This discovery rests on the recognition that for the application of medical MR magnets, steel having a magnetic permeability value of about 100 can still be considered unsaturated, and the steel will not be considered fully saturated until its value of magnetic permeability has dropped to about 50. Grade 1006 steel having a carbon content less that 0.06 atomic percent, and grade 1001 steel having a carbon content less than 0.005 atomic percent, exhibit the following magnetic permeability values at different field strengths:

| Field (Gauss) | Permeability Grade 1001 | Permeability Grade 1006 |
|---|---|---|
| 18,000 | 300 | 180 |
| 19,000 | 160 | 110 |
| 20,000 | 110 | 60 |
| 21,000 | 80 | 35 |
| 22,000 | 58 | 24 |

Thus, grade 1006 steel is usable up to around 20,000 gauss and grade 1001 steel is usable up to around 22,000 gauss. The magnets according to the invention can achieve field strengths significantly greater than one-half the saturation value of the ferromagnetic material used for the magnetic flux return path.

Figure 5A:
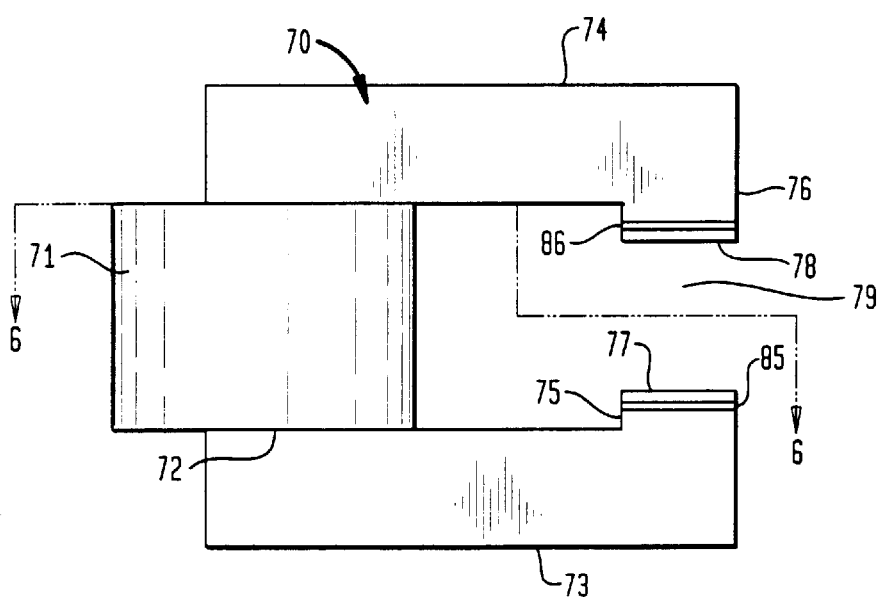
FIGS. 5A–5C are vertical elevations of magnets according to the invention which incorporate a C-shaped yoke.

FIG. 5A illustrates another magnet according to the invention which maximizes the open entry feature of the invention. The magnet is comprised of a C shaped ferromagnetic yoke 70 and an electromagnet coil 71 for generating a magnetic flux. The yoke 70 has a vertical portion 72 extending through the coil 71, and a pair of generally parallel legs 73, 74 each extending from an opposite end of the vertical portion 72 (see FIG. 6A). The ends 75 and 76 of the respective legs 73, 74 that are remote from the vertical portion 72 project toward each other and terminate at pole surfaces 77 and 78 which face each other and define a patient-receiving gap 79 between them.

Figure 5B:
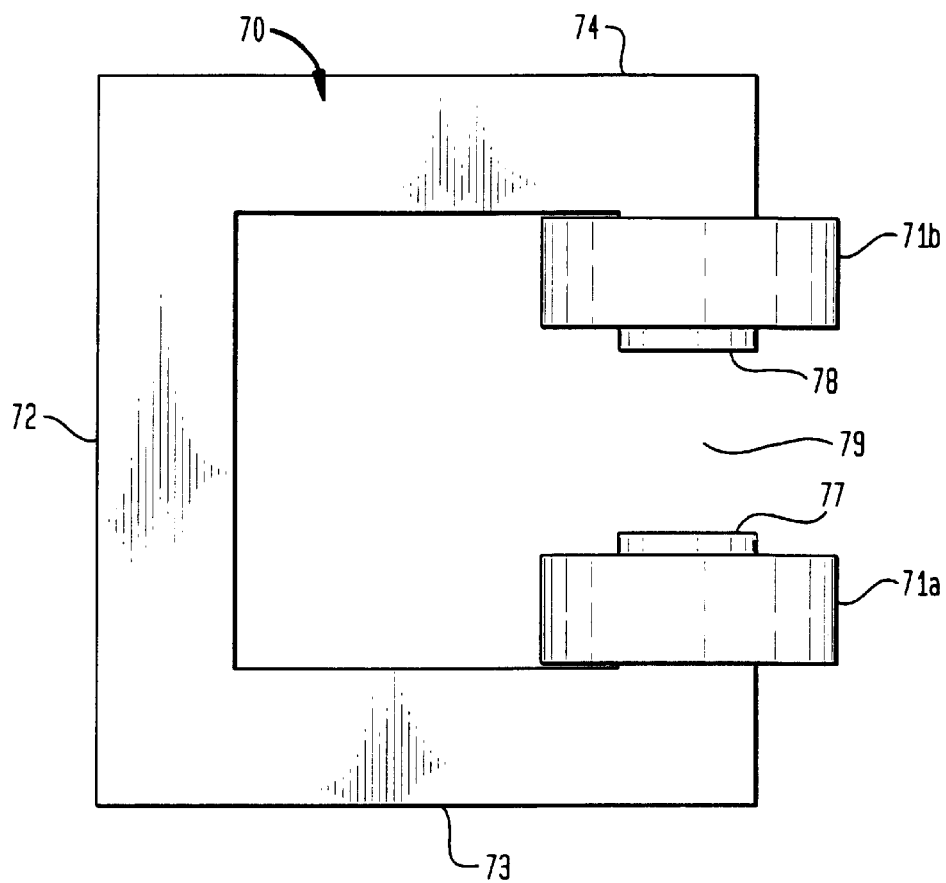

FIG. 5B illustrates another magnet having a C shaped yoke 70. The yoke comprises a vertical portion 72 and a pair of extending legs 73, 74 each terminating at a respective pole surface 77, 78. The patient receiving gap 79 is between the pole surfaces 77, 78 as in the previously described embodiment. Also, the pole surfaces 77, 78 are surfaces of the yoke 70, itself, and are the surfaces by which the magnetic flux enters into and leaves the gap 79, no separate poles apart from the yoke are required. Electromagnets 71a, 71b are disposed at the ends of the legs 73, 74 adjacent the pole surfaces 77, 78, respectively. The electromagnets 71a, 71b are advantageously superconducting in order to achieve high field strengths while allowing them to be light and compact. The magnets 71a, 71b need not be placed adjacent the pole surface as shown, but can be located anywhere along the lengths of the legs 73, 74 or the vertical portion 72.

The leg 74 is held above the leg 73 by only the vertical portion 72 of the yoke 70. As a consequence, access to the gap 79 is limited only by yoke vertical portion 72 and the coil 71 and by no other obstruction. The degree of open entry achieved by this structure can be appreciated from FIG. 6A which is a view taken along the section line 6—6 in FIG. 5A.

Figure 6A:
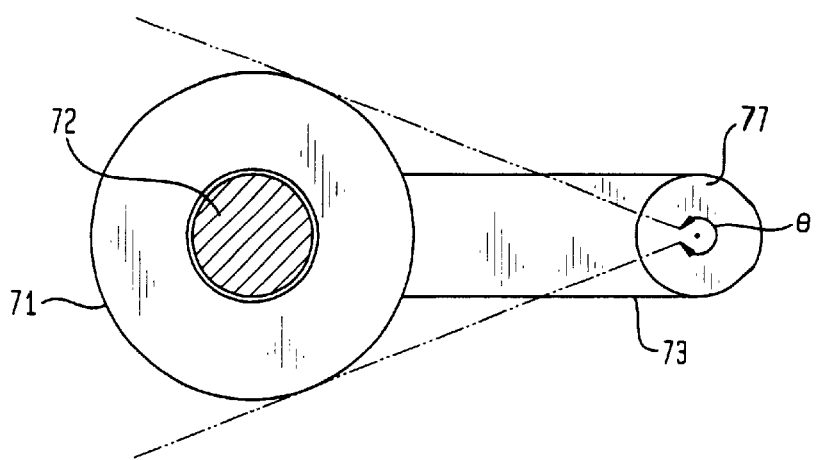
FIGS. 6A–6C are horizontal sections of magnet yoke structure having the open entry feature of the magnets according to the invention.

As shown in FIG. 6A, entry into the magnet gap 79 (FIG. 5A) can be along any direction within a continuous arc having an angular extent theta (0) which is limited by those directions of access which would intersect with other magnet structure, such as the coil 71 in the embodiment shown in FIG. 6A. The extent of unimpeded patient access is an arc greatly in excess of 180 degrees.

Figure 6B:
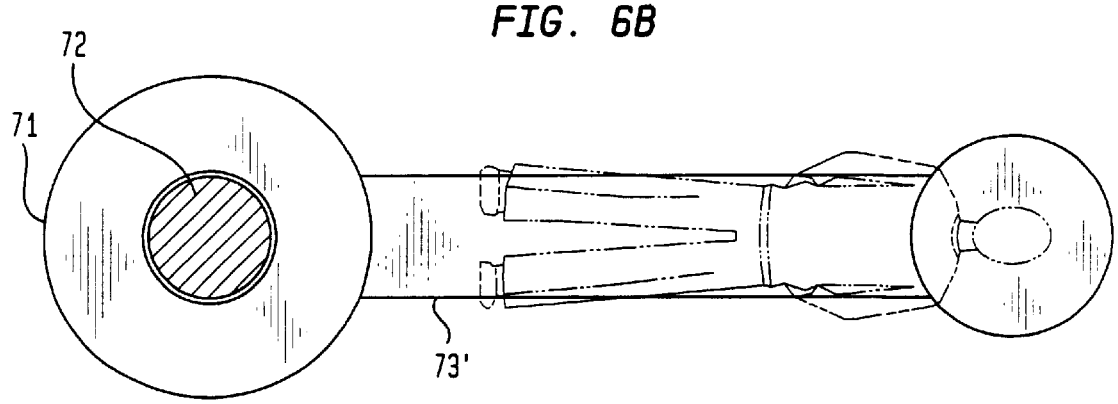

The open entry feature of the present invention is maximized by the embodiment shown in FIG. 6B. The illustrated magnet has a C-shaped yoke with greatly extended legs, the lower one 73' of which is shown. This permits a patient to be scanned lying fully extended along the leg 73' and to enter and leave the gap in the direction of the leg 73', and for attending medical personnel to have unobstructed access to the patient from all directions, while the patient is within the magnet gap. The illustrated embodiment also has a pole 80 for providing a pole surface facing the patient-receiving gap. The extent of unimpeded patient access in this embodiment is a full 3600 arc.

Figure 5C:
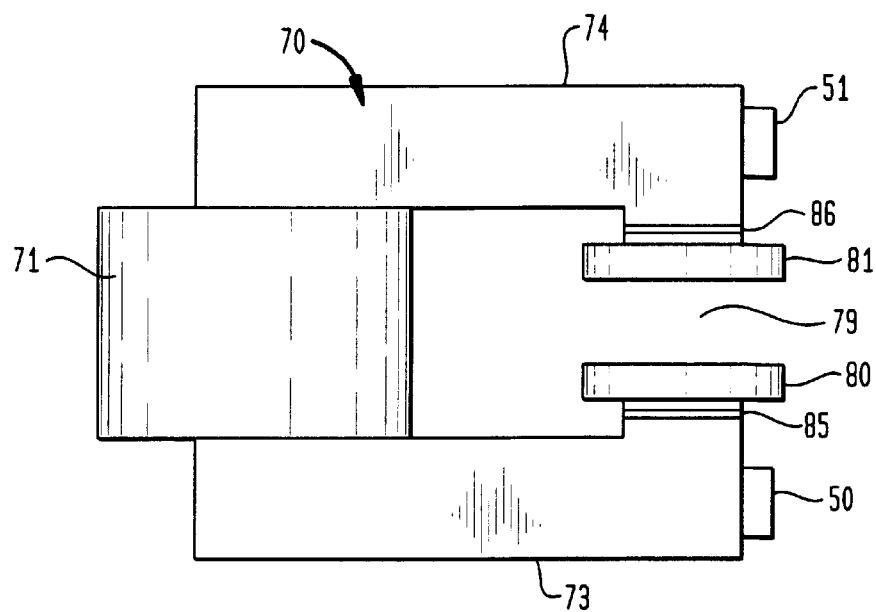
Figure 6C:
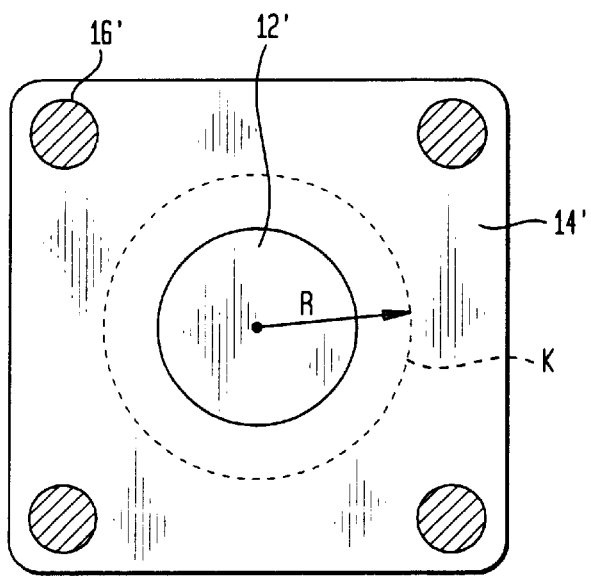

Another feature of the invention shown in FIG. 6C is the flux return structure in magnetic resonance magnets which is disposed to provide a continuous arc of unimpeded patient access whose dimensions or extent of unimpeded patient access is 90 degrees or greater. More particularly, means defining the ferromagnetic flux return path 14', 16' which extends between pole surfaces is configured so as to provide a continuous arc of a circle (the arc of patient entry shown as a dashed circle (k) in the drawing) for patient access through the arc to the patient-receiving gap whose center is the gap center, whose radius R is at least twenty-four inches, and which circle is also in the plane that is orthogonal to the direction of the main magnetic field and passes through the gap center and which continuous arc of entry provides unimpeded patient access to the gap between the pole surfaces, and which continuous arc of unimpeded patient access has an angular extent equal to or greater than 90 degrees. This feature is found in the embodiments shown in FIGS. 5A–5C and 6A, 6B of the application. It is also found in all magnets of the type illustrated in FIGS. 1–3, but having three instead of four columns. Magnets having four columns which are far enough away from the pole surfaces, and all embodiments of the invention covered by the claims herein having three columns, necessarily encompass the feature of providing unimpeded patient access over a continuous arc of 90 degrees or greater.

Magnets according to the invention having a C-shaped yoke further include additional magnet structure like that already discussed. FIG. 5C illustrates a pair of poles 80, 81 incorporated in a C-shaped magnet to provide pole surfaces which are wider than what the yoke structure, alone, can provide. The various embodiments of any eddy current suppressing means can likewise be incorporated into the magnet structure shown in FIGS. 5A–5C.

One feature characterizing the C-shape yoke is its asymmetry relative to an axis extending in the direction of the gap and through the center of the pole surfaces. For example, the legs 73, 74 which extend from the gap to the vertical portion 72 of the magnet yoke shown in FIG. 5A provide a large mass of ferromagnetic material which is not symmetrically distributed around the gap. This asymmetric distribution of ferromagnetic material will cause an undesired magnetic field gradient across the gap which will have to be compensated for by some means.

In the embodiment shown in FIGS. 5A–5C gradient compensation is achieved by providing a pair of gaps 85, 86 in the ends 75 and 76 of the respective legs 73 and 74. The gaps 85 and 86 are thin regions which are free of ferromagnetic material, although they are not necessarily air gaps. The magnetic reluctance in the gaps 85, 86 will be large relative to the reluctance asymmetries within the ferromagnetic yoke 70 so that the magnetic field distribution within the magnetic gap 79 will be predominately determined by the magnetic field distribution within the auxiliary gaps 85 and 86. The auxiliary gaps 85 and 86 will tend to smooth out the gradient which is caused by yoke asymmetry and consequently the magnet gap 79 will not exhibit such a gradient.

Figure 7:
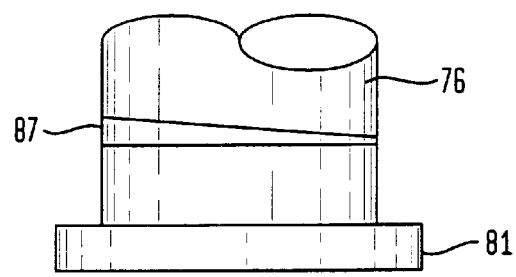
FIG. 7 illustrates a pole and auxiliary gap for magnetic gradient compensation.

The gradient caused by the ferromagnetic asymmetry of the yoke can be further improved by making the auxiliary gaps wedged shaped. In FIG. 7 the auxiliary gap 87 has a greater gap distance on the side of the magnet gap 79 which is closest to the yoke 70 than on the side of the auxiliary gap 87 which is furthest from the yoke 70. The magnetic flux path is not the same throughout the yoke 70 but is longest where the auxiliary gap 87 is largest, and conversely the magnetic flux path is shortest through the yoke 70 where the auxiliary gap 87 is narrowest. This wedge shape of the auxiliary gap 87 allows for the compensation of any gradient component resulting from the different magnetic flux path lengths within the yoke and thus achieves improved gradient compensation.

In the embodiments of FIGS. 5A–5C and FIG. 7, the auxiliary gaps need not necessarily be air gaps. They can be filled with a diamagnetic material such as aluminum and achieve their intended purpose. The inclusion of aluminum plates within the auxiliary gaps can facilitate the mechanical construction of the yoke, and help maintain the gap dimensions constant, to help achieve stability of the gradient compensating characteristics of these features.

This embodiment of the invention further includes auxiliary magnets 50 and 51. These magnets, which can be made of permanent magnet material, are located at the ends of the legs 73 and 74, respectively, of the magnet yoke 70. The auxiliary magnets 50, 51 develop magnetic fields, and the auxiliary magnets are oriented so that their magnetic fields oppose flux leakage from the ends of the yoke legs 73, 74. Consequently, they improve the magnetic field homogeneity within the patient receiving gap 79, and reduce magnetic field gradients within the gap 79 caused by asymmetrical distribution of the ferromagnetic material comprising the magnet yoke 70. They will also reduce magnetic field leakage and minimize fringing magnetic fields at the ends of the yoke legs 73, 74.

Figure 8:
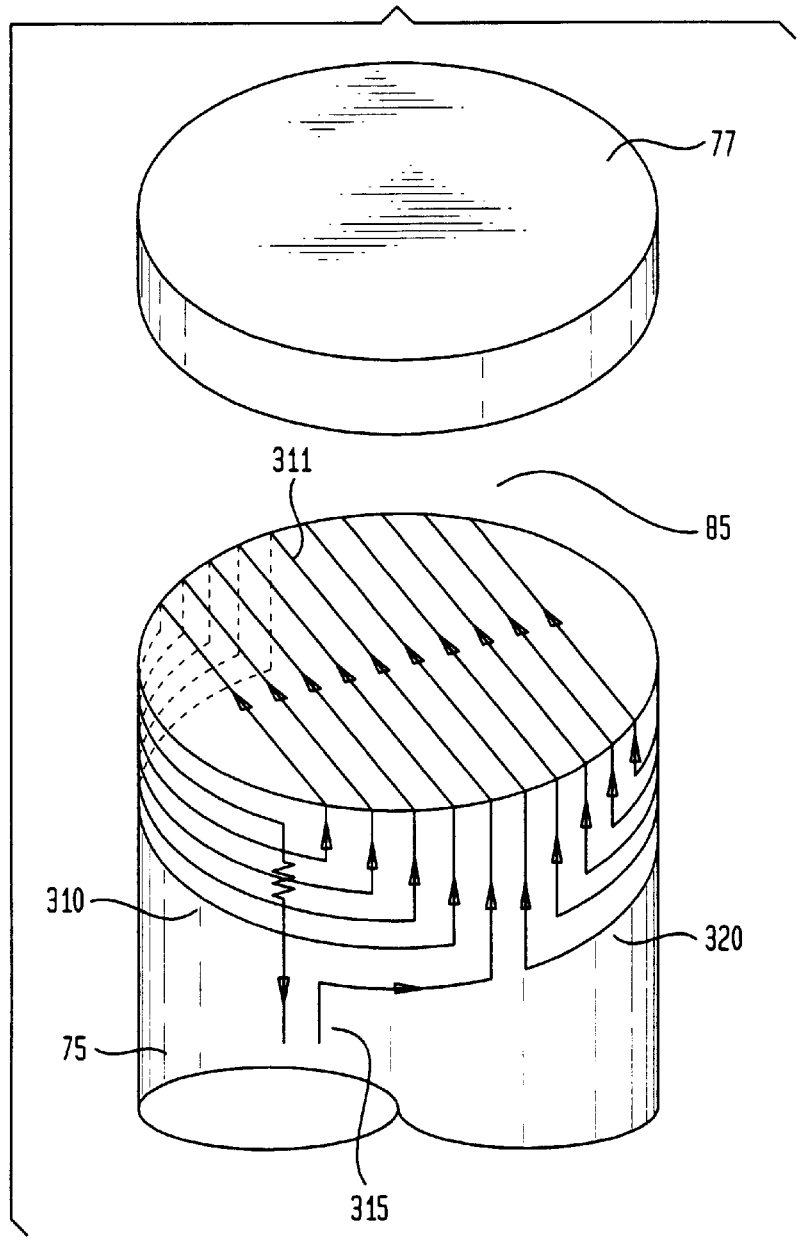
FIGS. 8 and 9 illustrate poles and compensating coils for magnetic gradient compensation.
Figure 9:
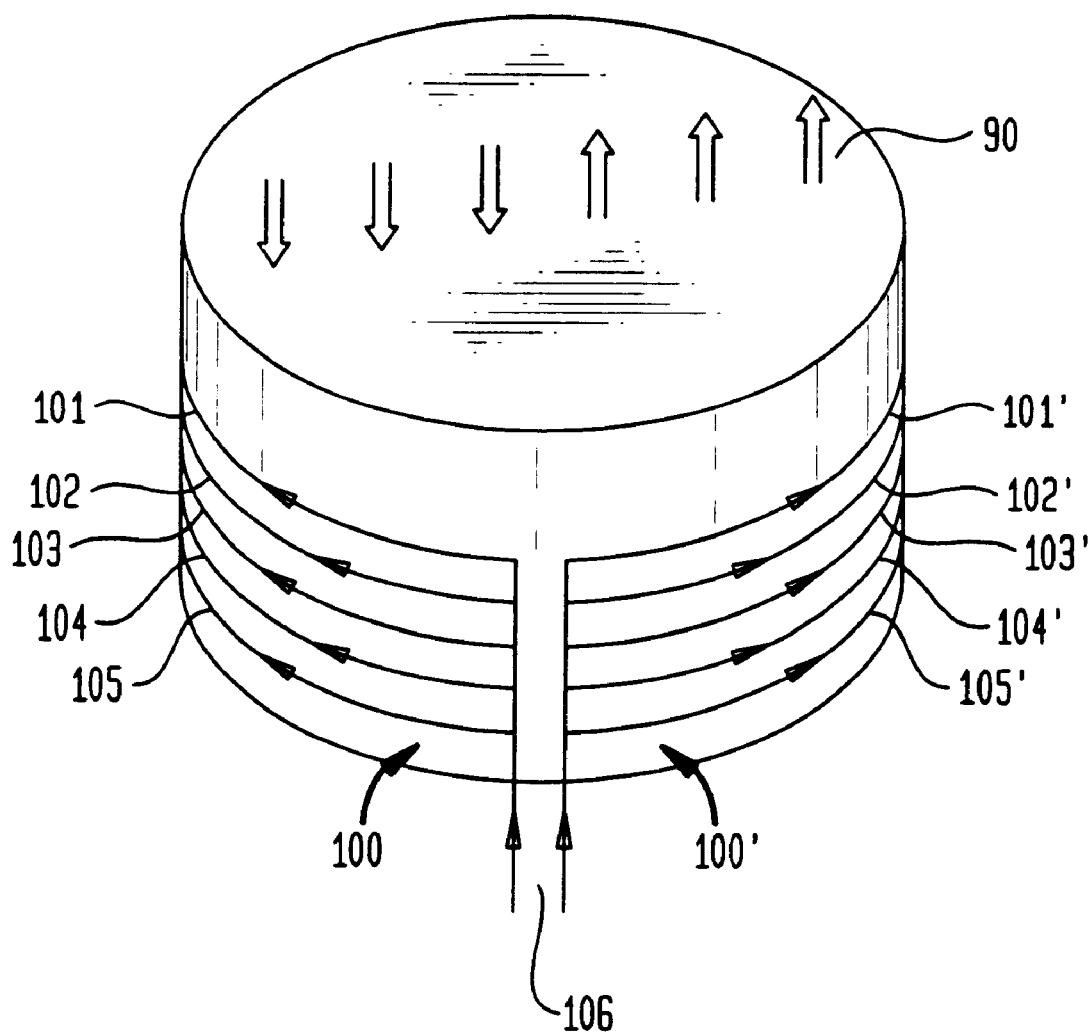

FIGS. 8 and 9 illustrate two structures for electrically compensating for the undesired gradient which occurs in magnets having C-shaped yokes. In FIG. 8 auxiliary gaps 85, 86 of FIGS. 5A, 5C have a gradient compensating coil disposed between the surfaces of air gaps 85, 86.

FIG. 8 is an exploded view of the end 75 of the leg 73 of the C-shaped yoke 70 shown in FIG. 5A. The pole face 77 is separated from the rest of the leg end 75 by the auxiliary gap 85 which has been provided for compensating for magnetic field asymmetry within the patient-receiving gap 79, as previously described. In order to further improve field asymmetry compensation, a pair-of gradient-producing coils 310 and 320 is provided within the auxiliary gap 85. Coil 310 is comprised of a plurality of segments 311 across the gap 85 which are connected in series and which terminate at current lead-in pair 315. The coil 320 has identical structure but is a mirror image of coil 310. When currents flow through the coils 310 and 320, a magnetic gradient field is developed within the auxiliary gap 85 which can be varied to cancel the field asymmetry within the patient-receiving gap 79. The segments of the coils which cross the auxiliary gap 85 are shown as straight cords, but they can be arcuate to modify the gradient field, if desired.

FIG. 9 illustrates a compensating coil pair 100, 100' on the side of the pole 90. The compensating coil 100 is comprised of individual conductors 101–105. The structure of the compensating coil 100' is symmetrical to that of compensating coil 100, and comprises individual conductors 101'–105'. A current lead-in pair 106 delivers current to the compensating coils 100 and 100', and an identical pair (not shown) on the opposite side of the pole 90 provides a current outlet. Because the currents, depicted by arrows, in the respective coils 100 and 100' flow in an opposite sense around pole 90, the resulting magnetic field will be a linear gradient field which is zero on the pole diameter between the compensating coils 100 and 100'. The gradient field is depicted by broad arrows in FIG. 9. This particular arrangement is advantageous because, although a gradient field is generated, the net change in magnetic field within the magnet gap is zero. Thus, the current through the compensating coil will induce a gradient for gradient correction, while leaving the net field within the gap substantially unchanged. Moreover, even order terms of the field cancel so that the field will be purely an odd function.

A further means for compensating the expected magnetic field gradients arising from the ferromagnetic asymmetry of the C magnet would be to obtain field maps of the imaging volume utilizing either a Hall probe or an NMR Teslameter to determine three dimensional spatial field values in the imaging volume; and deriving from the maps, which once determined would be permanent with respect to the C-magnet asymmetry, a table of magnetic field correction values to apply a software correction for the pixel frequencies of the imaging volume to cope with the C magnet gradient. Mapped magnetic field values convert to pixel frequencies by the Larmor relation $\omega = \gamma H_o$ where $\omega$ is the pixel frequency, $\gamma$ is the gyromagnetic ratio of the imaging nucleus and $H_o$ is the magnetic field value.

Aside from their larger gap size, the embodiments of the invention discussed up to now have not been specified as to their overall size. Conventionally, the magnet yoke has been made just large enough to house the magnetic flux generating means and provide patient access. In addition, the present invention includes additional preferred embodiments having dimensions which are greater than dimensions of magnets built to date. For the case of magnets having spaced pole supports spaced by columns, such as shown in FIGS. 1–3, the column height, i.e. the space between the pole supports is greater than 60 inches, and the radius from the gap center to the nearest piece of yoke structure is greater than 45 inches. In the case of magnets with C-shaped yokes with a vertical field (FIG. 5B), the vertical portion of the frame 72 is at least 48 inches, and the horizontal legs 73, 74 are at least 36 inches long. In the case of magnets with C-shaped yokes with a horizontal field (FIG. 12), the horizontal portion 138 is at least 48 inches, and the distance L1, L2 from the pole faces to their respective vertical legs is at least 10 inches. The inventions disclosed herein can also be physically realized with much larger dimensions that will permit patients and assisting personnel to stand within the magnet yoke as is discussed later.

Scanning Facilities

Figure 10:
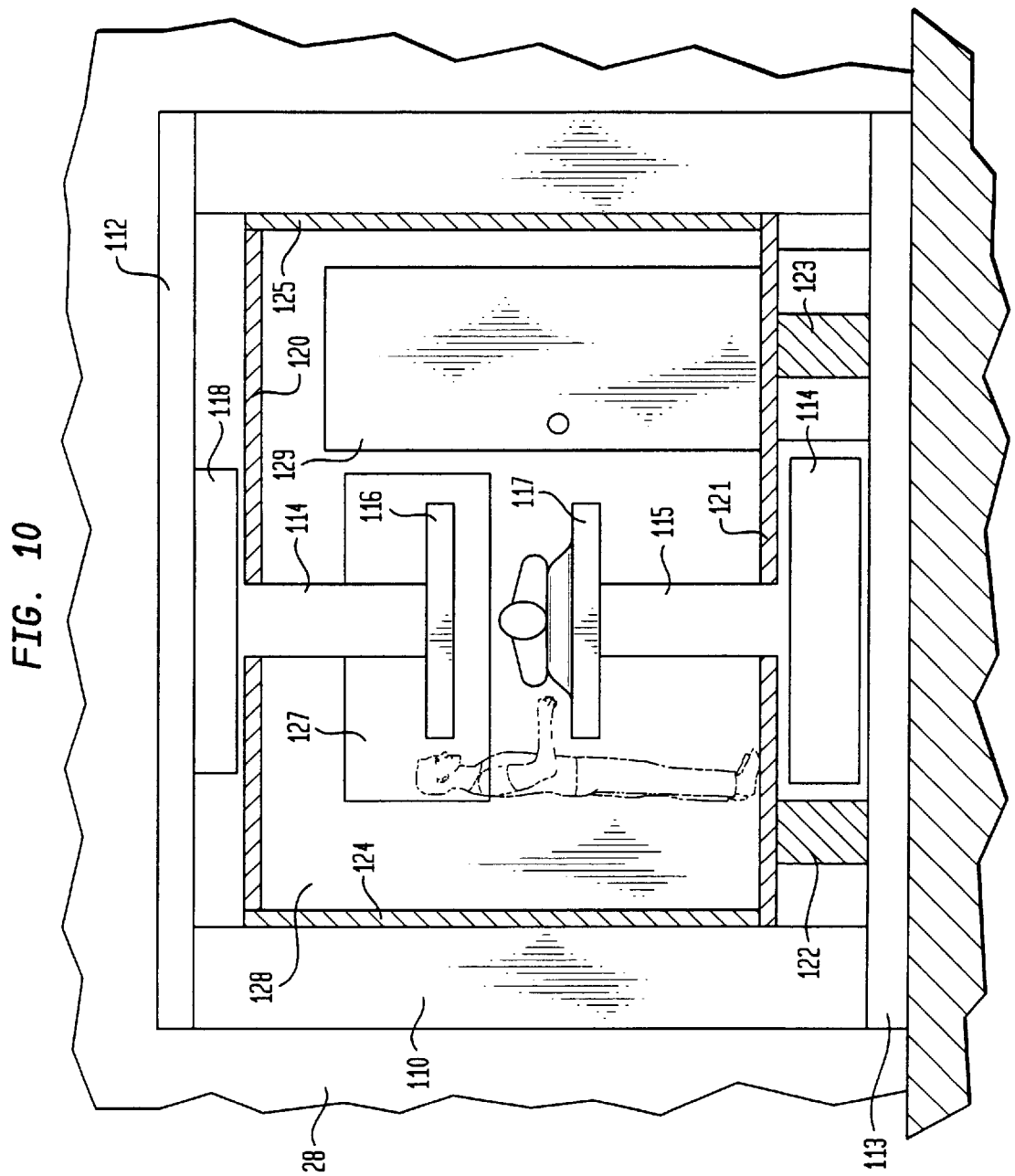
FIGS. 10 and 11 illustrate magnetic resonance scanning facilities incorporating magnets according to the invention.

FIG. 10 illustrates an MR magnet according to the invention which is sufficiently large to allow people to stand within the magnet yoke, and which has built into it a room which hides the magnet structure from view. The magnet is comprised of at least three columns, two of which, 110, 111 are shown. Upper and lower pole supports 112, 113 are disposed at opposite ends of the columns, in the manner previously described. The columns and pole supports are ferromagnetic material as in the earlier described embodiments. The dimensions of the yoke components are somewhat arbitrary, but in the illustrated embodiment the columns are approximately 8 to 9 feet in length, and the pole supports are around 12 feet wide. Pole stems 114, 115 respectively support poles 116 and 117 in the manner previously described. Sources of magnetic flux 118, 119 are also provided.

The magnet rests on and is supported by a structural floor or foundation 120. Within the magnet yoke a false floor 121 is maintained elevated above the lower pole support 113 by supports 122, 123. The false floor 121 provides the surface upon which people stand while they are within the magnet yoke. Internal wall panels 124, 125 and a false ceiling 126 together comprise an internal room within the magnetic yoke which shields the yoke structure from the view of people within that room. A front wall 128 and a rear wall (removed in FIG. 10) completes the room within the magnet yoke. The front wall 128 includes a door 129 for access into the gap room, and a window 127 for viewing a patient while in the magnet gap.

This particular embodiment provides the maximum in open entry; the directions in which the gap can be entered or exited cover a continuous 360 degree arc. Moreover, any claustrophobic reaction is also minimized since there are no lateral obstructions on any side of the patient, only the pole facing the patient. Additionally, the patient can be easily attended by medical personnel for placement into and removal from the gap, and while the patient is within the gap.

The combination of a magnet and a room large enough to walk into, which hides most of the magnet yoke structure from view, creates a scanning facility that provides an extremely high degree of access to a patient within the magnet gap, and also permits new combinations of medical procedures to be used in connection with magnetic resonance studies. In particular, the scanning facility comprised of a room large enough to stand within and housing a magnet gap can be used as an operating room in which to conduct magnetic resonance guided surgery.

Figure 11:
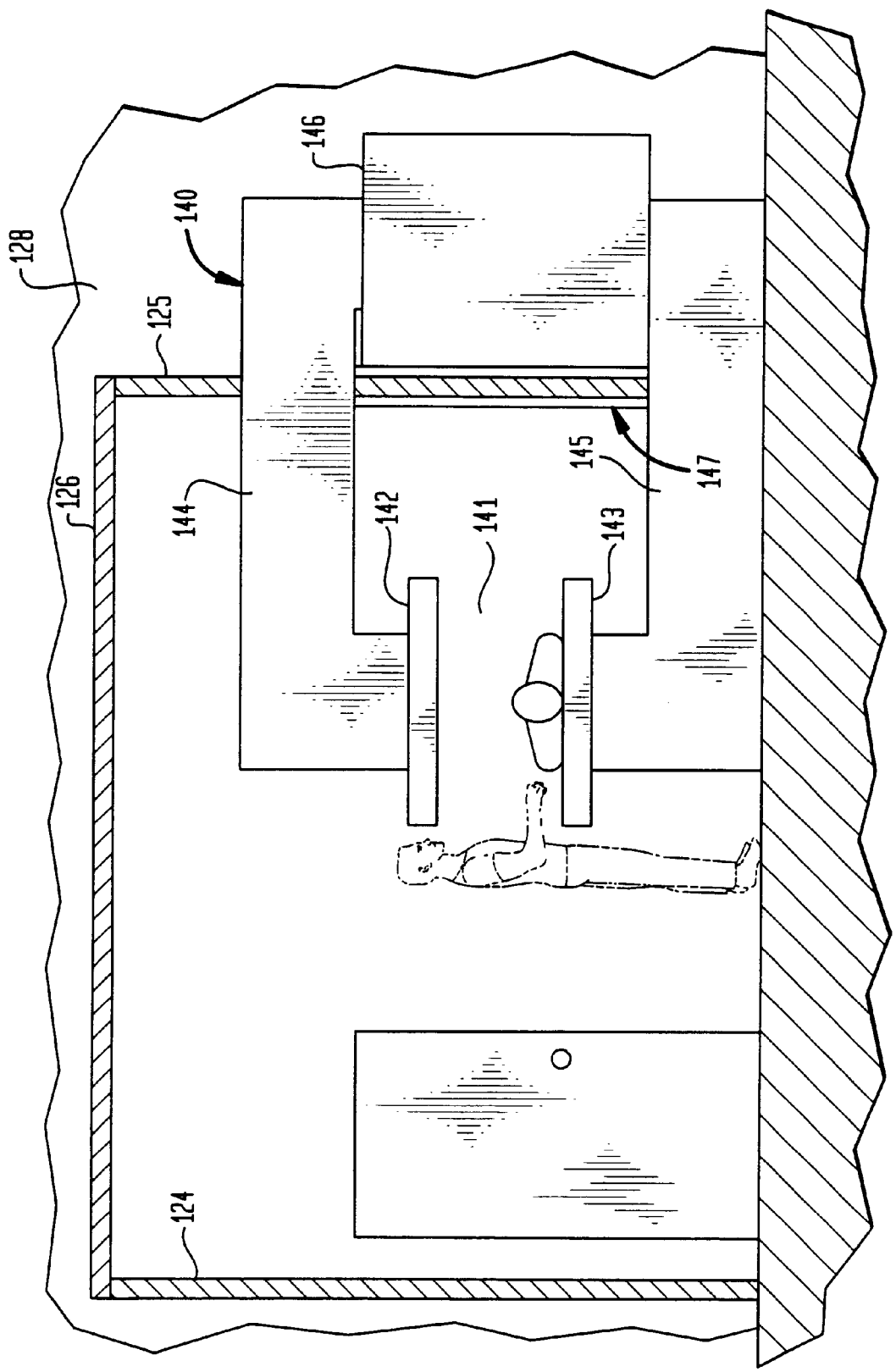

FIG. 11 illustrates another scanning facility which incorporates a magnet 140 having a C-shaped yoke. A room comprised of walls 124, 125 and ceiling 126 and front wall 128 encloses the patient-receiving gap 141 which is between the magnet poles 142 and 143. The legs 144 and 145 of the magnet yoke extend through the wall 125 so that the electromagnet 146 is outside of the room housing the gap 141. Magnets with C-shaped yokes like that shown in FIG. 5B, with a pair of electromagnets adjacent the pole surfaces can also be incorporated in this sort of scanning facility. In such a case the electromagnets would be within the room along with the pole surfaces. In addition to the self supporting yoke of the C-magnet of FIG. 11 the embodiment may optionally include non-ferrous support structures 147 to aid in supporting the poles.

All of the MR magnets according to the invention have been shown with vertical magnetic fields. However, for some applications a horizontal magnetic field may be preferred. One way of realizing horizontal field magnets for magnetic resonance and having ferromagnetic yokes is to orient the previously described structure, properly dimensioned, at right angles relative to the orientation shown in FIGS. 10 and 11 so as to generate a horizontal magnetic field. Additionally, ferromagnetic yoke magnets may be specifically constructed and configured to operate with a horizontal magnetic field, and configured to carry out particular magnetic resonance studies.

FIG. 12 illustrates a medical MR magnet having a C-shaped ferromagnetic yoke with the magnetic field oriented horizontally. The yoke 130 carries a pair of poles 132, 133 for establishing a horizontal magnetic field. Auxiliary gaps 134 and 135 are provided for compensating inherent gradients generated by yoke asymmetry. The coil 131 used to generate magnetic flux is beneath a false floor 136 so that a patient can simply walk between the poles 132 and 133 for positioning prior to undergoing a magnetic resonance study. A body rest 137 shown generally vertically oriented is provided within the gap and is mounted to pivot between the vertical orientation shown and a horizontal orientation. A pair of upstanding vertical supports 151, 152 are positioned with the body rest 137 between them. The body rest 137 is mounted on the supports 151, 152 by a pair of pivots 153, 154. Body rest 137 may also possess a seat shown by dashed line to sit the vertically oriented patient when desired.

A horizontal platform 155 at the lower end of the body rest allows a patient to stand on the platform and to lean against the body rest to facilitate patient immobilization within the gap. This configuration of a horizontally oriented magnetic field in a medical MR magnet having open entry results in a very convenient configuration. This magnet configuration is suitable for use in screening studies as well as the usual studies carried out by magnetic resonance. Additionally it provides for MR studies of the upright patient where the studies can be performed while the human body, spine, joints, central nervous system and other organs are acted upon by the gravitational field, loading it as it normally loads the upright human body.

FIG. 13 shows the body rest 137 pivoted upward to a generally horizontal position with a patient lying face down on the body rest. The body rest 137 can be moved between horizontal and vertical and held horizontal by any convenient mechanism such as a clutch mechanism to permit a magnetic resonance study to be carried out with the patient horizontal. It is particularly advantageous in some circumstances to position the patient face down in a prone position. For example, magnetic resonance imaging of the spine during spine surgery, and breast imaging, and other magnetic resonance studies of those parts of a patient's anatomy that are advantageously studied with the patient prone.

Figure 14A:
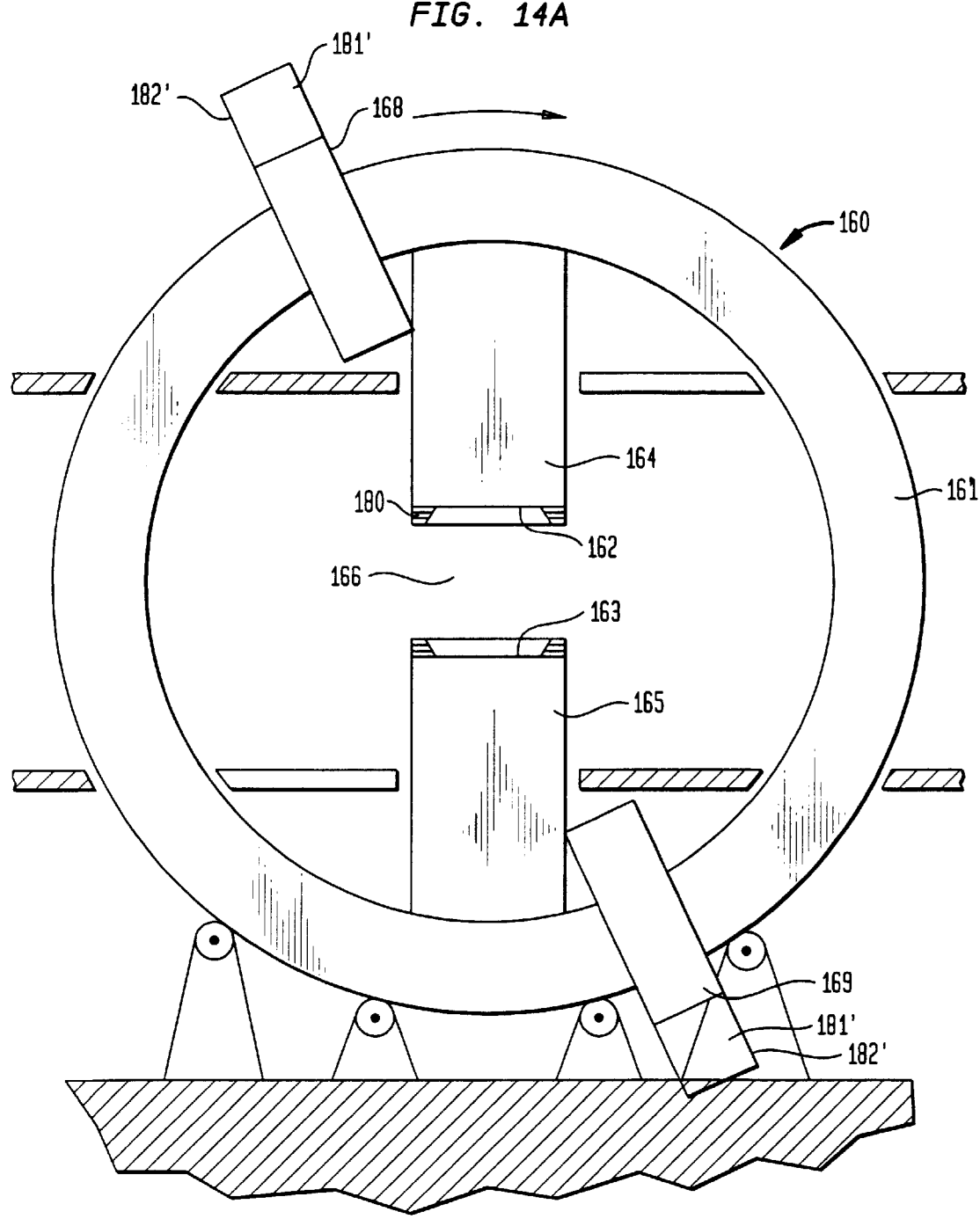
FIGS. 14A, 14B, 14C and 14D illustrate embodiments of magnets according to the invention which have a rotatable magnetic field.

It would be desirable to have available both a vertical magnetic field magnet and a horizontal magnetic field magnet in the same scanning facility. FIG. 14A illustrates part of a scanning facility having a magnet having a variable magnetic field direction that can vary between vertical and horizontal.

The magnet 160 is comprised of a ring-shaped ferromagnetic yoke 161 having a pair of opposing pole faces 162, 163. Each of the pole surfaces 162, 163 is at the end of a respective one of the poles 164, 165 and the poles 164, 165 are fixed to the yoke 161. The patient-receiving gap 166 is between the pole surfaces 162, 163. The ring-shaped yoke 161 is supported vertically and mounted for rotation about its center on rollers 167. One of the rollers can be driven so that rotation of the driven roller will cause the ring-shaped yoke 161 to turn. Magnetic flux generating means is comprised of a pair of electromagnets 168, 169 which are fixed and which clear the yoke 161 to allow it to freely turn. The electromagnets 168, 169 are preferably superconductive magnets, although they could be resistive magnets. Alternatively, they could be stacks of permanent magnet material.

The electromagnets each develop a flux which flows through the yoke 161. The currents through the electromagnets are selected so that the flux from each magnet flows through the yoke in a direction opposite the flux from the other electromagnet. A consequence of the opposing flux directions is that the flux is forced out of the ring-shaped yoke and through the poles 164, 165 and across the gap 166. In this way magnetic flux is provided in the patient-receiving gap 166 for carrying out a magnetic resonance study on a patient.

When the yoke 161 is rotated the poles 162, 163 rotate with the yoke and the magnetic field within the gap rotates with the poles. Thus, the vertical magnetic field developed with the magnet oriented as shown in FIG. 14A will become a horizontal magnetic field when the yoke 161 is rotated through 90 degrees. This magnet structure thus allows for selection of the magnetic field direction depending upon the MR study to be carried out and upon the MRI directed surgical treatment to be conducted in connection with the MR study.

Figure 14B:
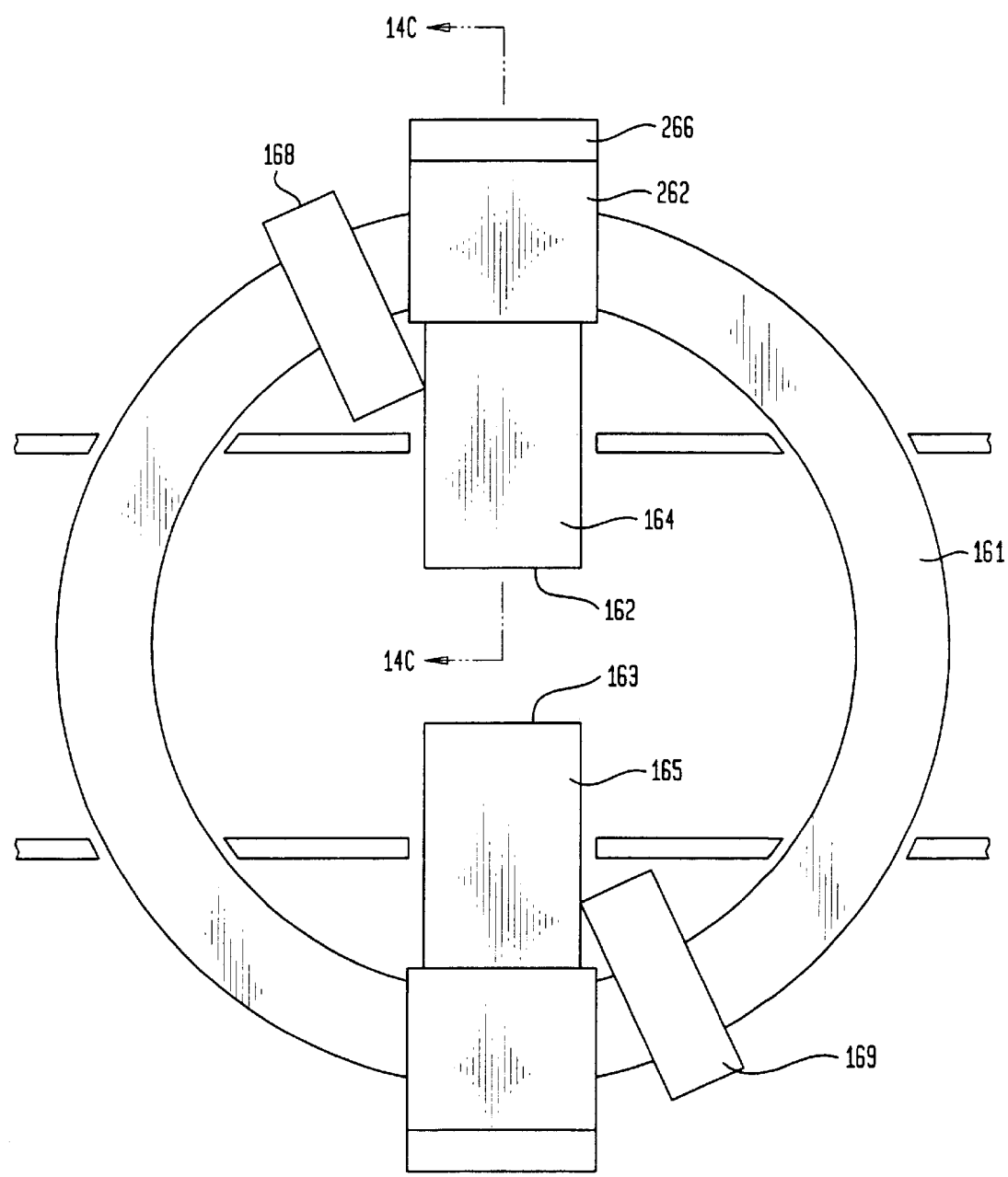

In FIG. 14B the ring-shaped yoke 161 remains stationary, and the poles 164, 165 rotate on the yoke 161. Magnetic flux generating means 168, 169 develops magnetic flux which flows through the yoke 161, the poles 164, 165 and the patient-receiving gap 166 as previously described. In the embodiments of FIGS. 14A, 14B flux generating means 168, 169 may also be mounted on the poles 164, 165 in the same manner as in FIG. 5B.

Figure 14C:
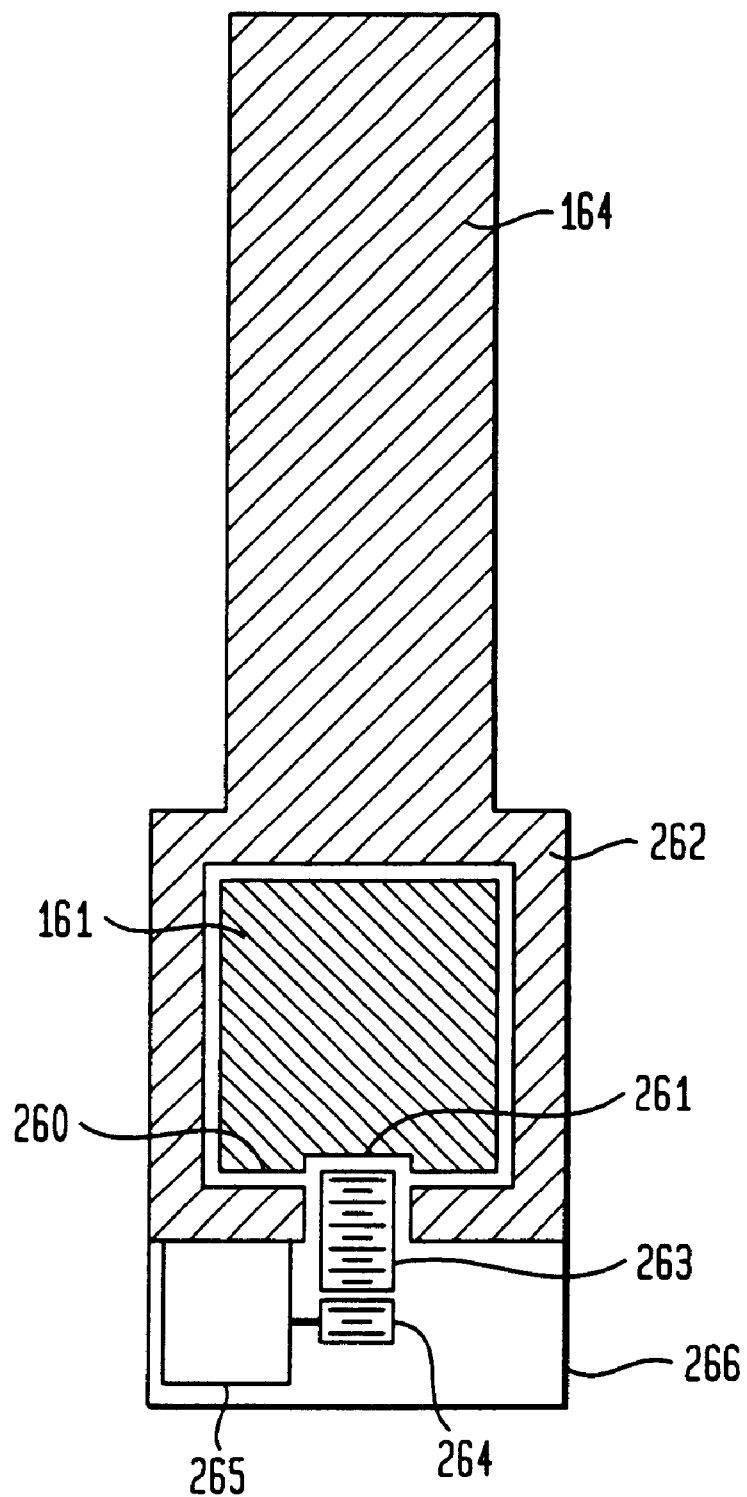
Figure 14D:
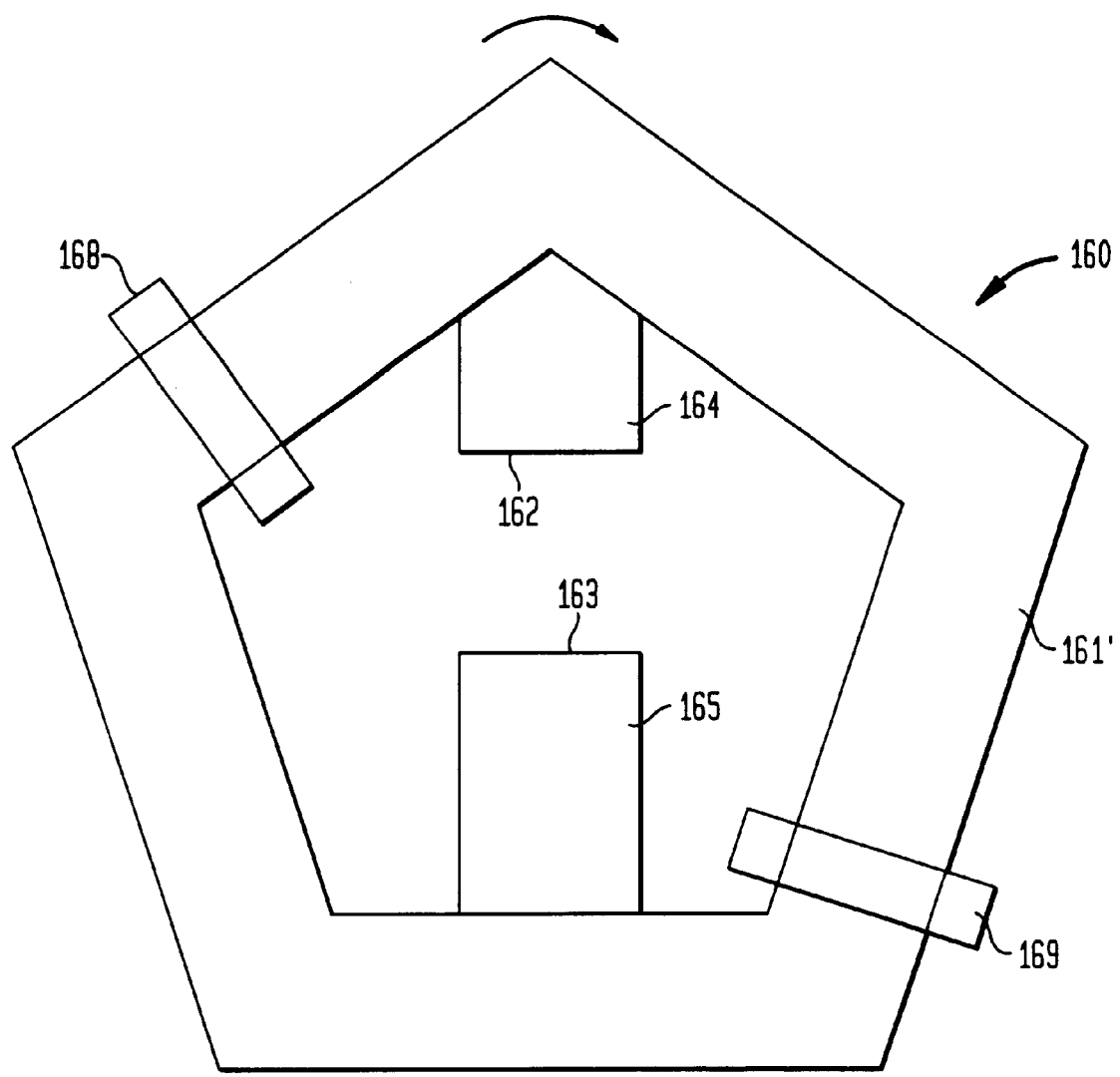

FIG. 14C illustrates structure for rotating the magnet poles on the ring-shaped yoke 161 in order to change the orientation of the magnetic field without having to rotate the yoke. The yoke 161 has a square cross-section. The outer circumferential surface 260 of the yoke 161 has an integral train of gear teeth extending around the part of the yoke 161 along which the pole 164 is intended to travel. The pole 164 has a collar 262 that engages the yoke 161 and allows the pole to travel along the circumference of the ring-shaped yoke 161. A gear 263 engages the gear teeth 261 of the yoke and is mounted for rotation on the collar 262. A second gear 264 engages the gear 263, and the second gear 264 is driven by a motor and speed reduction mechanism 265. The gears and motor are housed within a cover 266.

When the motor 265 is operated to drive the gear 264, the gear 263 mounted on the collar 262 is in turn driven to rotate. Rotation of the gear 263 causes the gear to travel along the train of gear teeth 261, and causes the pole collar 262 and pole 164 to travel along with the gear 263. The direction of travel of the pole is selected by selection of the direction of rotation of the gear 264 by the motor 265. In this way, the need to rotate the entire yoke 161 and the flux generating means 168, 169 to change the magnetic filed orientation is obviated.

Figure 15:
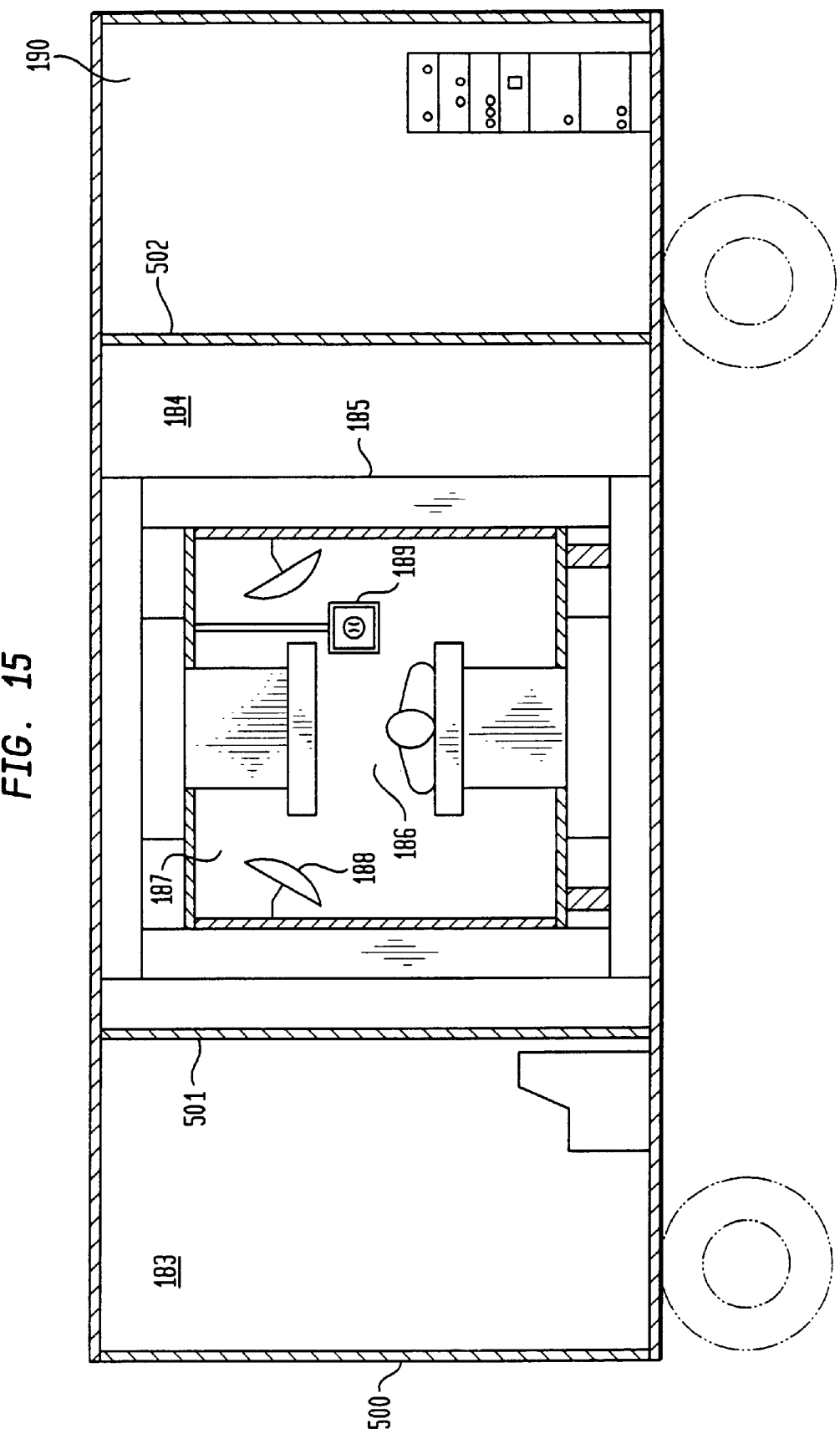
FIG. 15 is a side view, in vertical section, of a mobile facility according to the invention for carrying out magnetic resonance guided surgery.

In order to deliver magnetic resonance imaging directed surgical treatment, a surgical facility with an integral MR magnet can be made mobile. FIG. 15 shows a vertical section of a vehicular facility containing an operating room with an MR magnet.

The vehicle body 180 has internal walls 181, 182 dividing the body interior into three compartments 183, 184, 185. Compartment 183 is used to house an operator's console for a magnetic resonance scanning system, and compartment 185 is used for racks of electronics equipment and any other ancillary equipment present. Compartment 184 houses a magnet 185 for the magnetic resonance scanning system and the equipment for an operating room.

The magnet 185 within the compartment 184 is sufficiently large to permit a surgeon and other medical personnel to stand within it to operate on and attend to a patient that is within the patient-receiving gap 186 of the magnet 185.

In the particular embodiment illustrated, a false floor and ceiling and walls create an operating room 187 within the magnet as has been previously described. The operating room is equipped with facilities necessary for carrying out surgical treatments, such as high intensity lighting 188 and a monitor 189 for displaying images of patient anatomy acquired by magnetic resonance imaging. The structure creating the operating room 187 within the compartment 184 is not strictly essential. If the compartment 184 can be kept sterile, then it can serve as the operating room.

Magnetic Resonance Scanning Techniques

Figure 16:
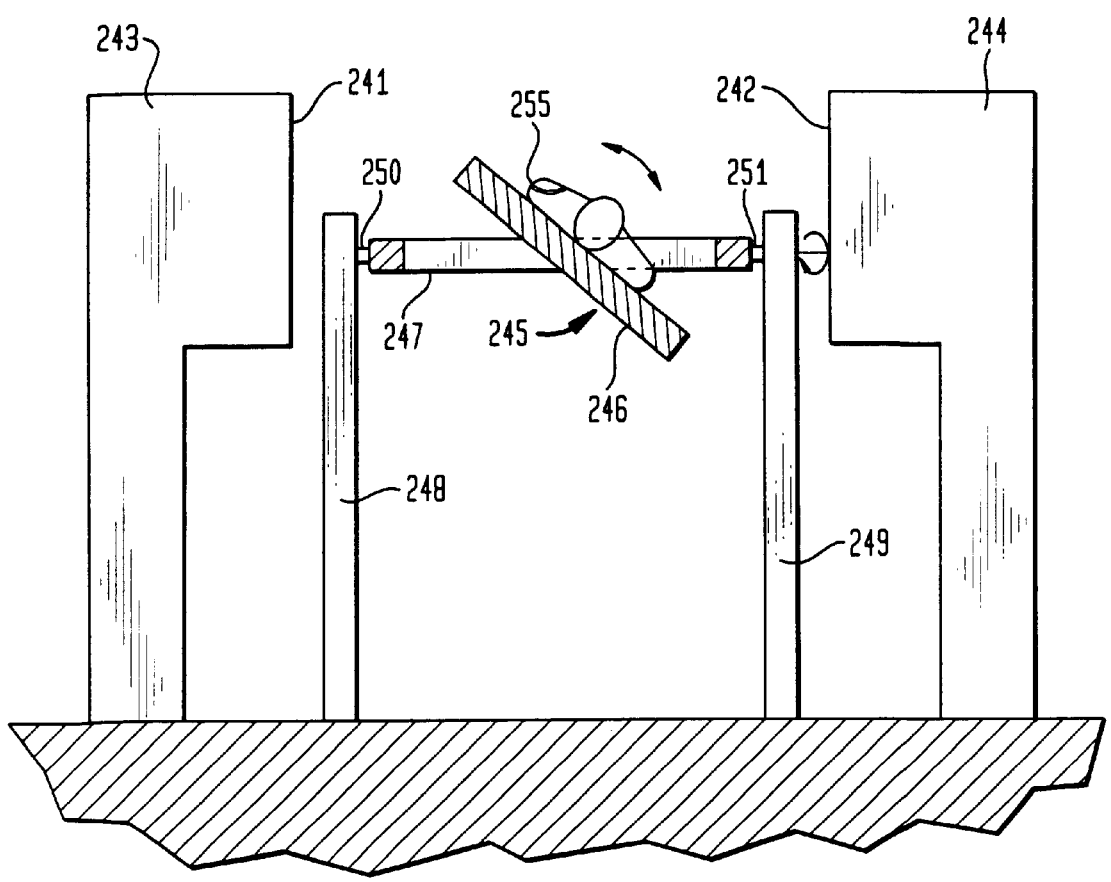
FIG. 16 is a magnet according to the invention having a patient support and positioning device for orienting the patient within the patient-receiving gap of the magnetic.

In FIG. 16 a pair of pole surfaces 241, 242 define a patient-receiving gap between them. The pole surfaces 241, 242 are formed on yoke portions 243, 244, respectively, of a magnet yoke which is oriented to develop a horizontal magnetic field. The patient-receiving gap is between the pole surfaces 241 and 242. A patient supporting and orienting apparatus 245 supports the patient within the patient-receiving gap and determines the orientation of the patient within the gap.

The patient supporting and orienting apparatus 245 is comprised of a patient rest 246 which is elongated to permit a patient to lie on it in a fully extended position. The patient rest 246 is situated within a frame 247, and is mounted within the frame 247 to pivot about its longitudinal axis. This structure allows the patient to be tilted within the patient-receiving gap as shown in the drawing and indicated by the double-headed arrow.

The frame 247 is supported by a pair of vertical supports 248, 249 which support the frame 247 by a pair of pivots 250, 251. The pivots 250, 251 permit the frame 247 to pivot around an axis extending through the pivots, and tilt the patient rest 246 and any patient thereon, within the gap.

In the drawing the patient is shown having a radio-frequency surface coil 255 disposed on his shoulder region. The patient supporting and orienting apparatus 245 allows the patient to be oriented, and the RF surface coil 255 to be oriented along with the patient. The RF surface coil 255 is oriented relative to the magnetic field of the magnet in order to maximize the received magnetic resonance signal.

The incorporation of the patient supporting and orienting apparatus is made possible because of the open entry feature of the magnet according to the invention, and because of the large gap size achieved in this invention. Both open entry and large gap size are, in turn, made possible by the use of ferromagnetic flux returns in the magnet according to the invention.

Figure 17:
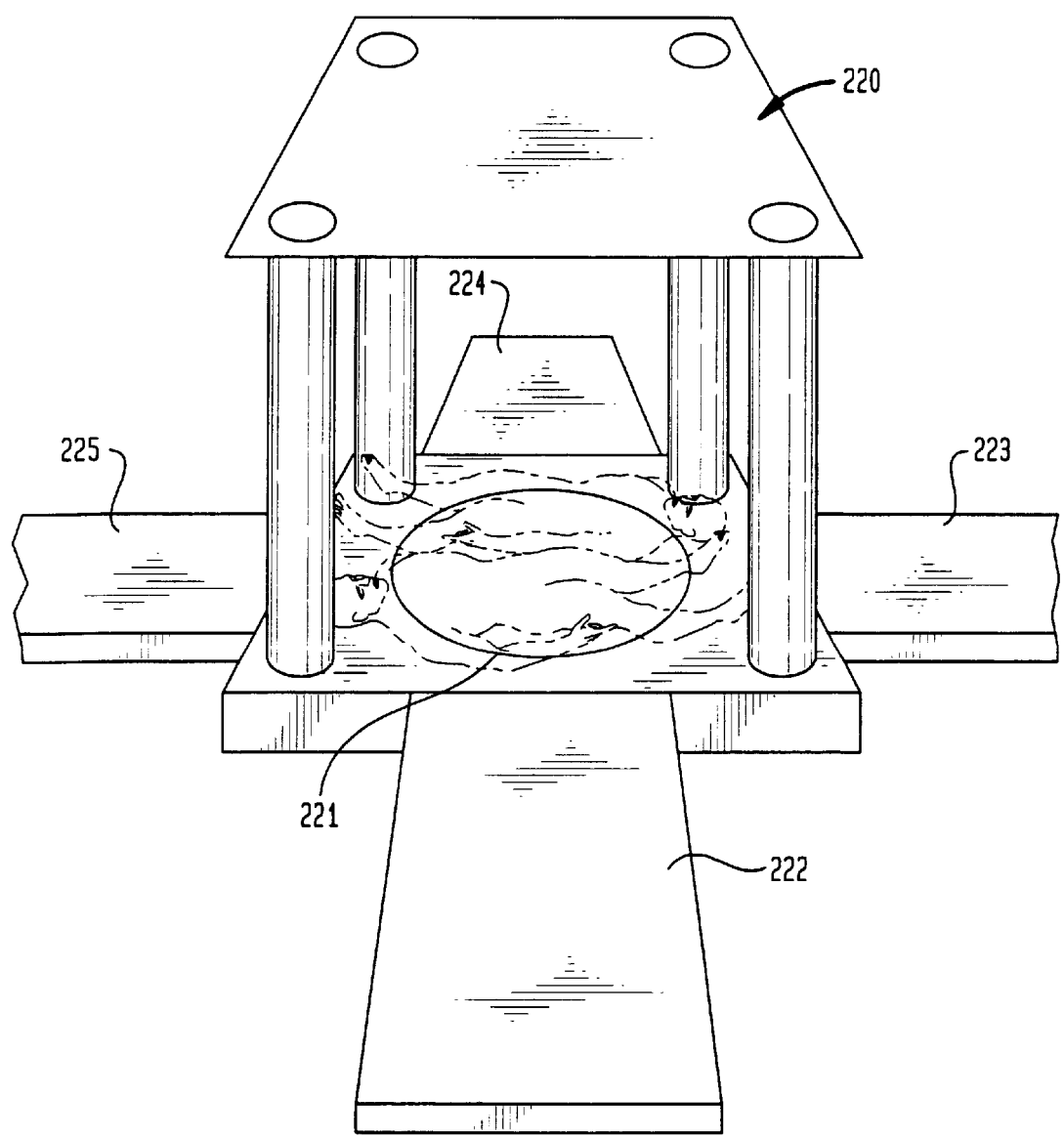
FIGS. 17, 18A and 18B show open access magnets according to the invention used for multi-patient scanning.

FIG. 17 is an isometric view of an open entry magnet according to the present invention which has been configured for scanning multiple patients. The magnet develops a vertical field and is comprised of a yoke 220 having a pole surface 221 which is accessible by more than one non-collinear direction. Four patient supports or beds 222-225 are arranged around the magnet and are aligned along the directions of entry into, and egress from, the patient-receiving gap of the magnet. In particular, the beds 222 and 224 are aligned along one entry direction and the beds 223 and 225 are aligned along the other entry direction.

The diameter of the pole surface 221 is large enough to simultaneously accommodate more than one patient in the patient-receiving gap, and to allow scanning of one or more than one patient at the same time, when more than one patient is simultaneously within the gap. The patients shown within the magnet are both positioned for torso scans, but different patients may have different parts of their respective anatomy within the gap for scanning at the same time.

Figure 18A:
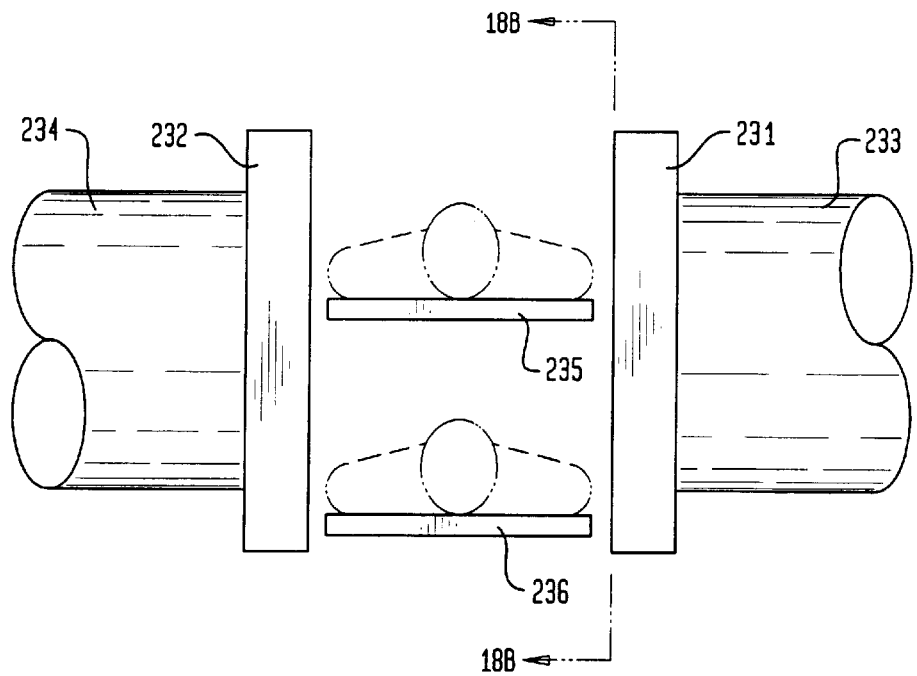

In FIG. 18A multiple patients are simultaneously located within a horizontal field open entry magnet. The patients are positioned one above the other. The pair of magnet poles 231, 232 are spaced to develop a horizontal magnetic field, and each of the poles is attached to respective parts 233, 234 of the magnet yoke. The patients are positioned within the patient-receiving gap on horizontally extending patient supports. The upper patient support 235 is roughly along the horizontal diameter of the poles, although this position is arbitrary and the support 235 can be positioned higher or lower as may be desired. The lower patient support 236 is roughly adjacent the pole edge, but this is also arbitrary and the lower patient support 236 can also be positioned higher or lower as desired.

Figure 18B:
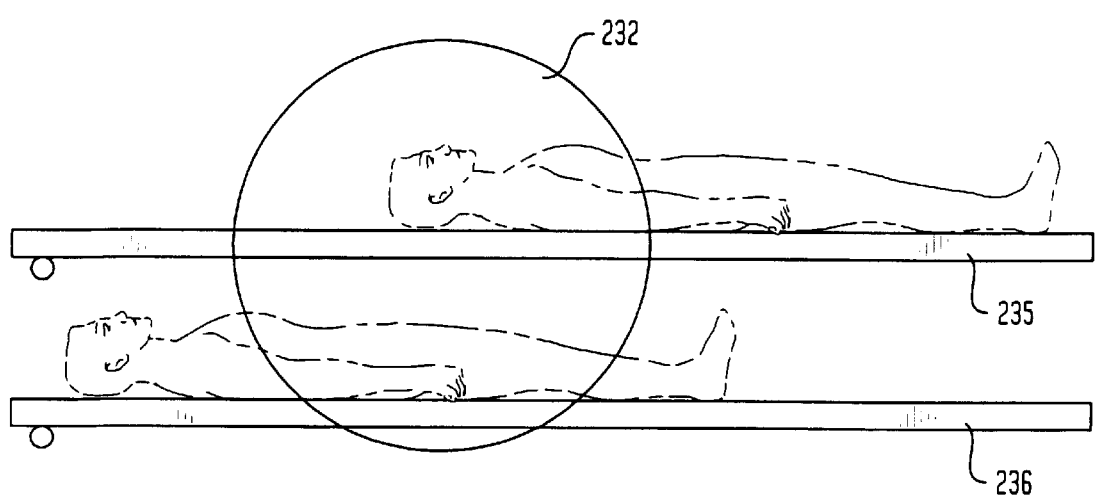

FIG. 18B is a vertical section taken along the section line 18B—18B in FIG. 18A. The positions of the patients along the lengths of their respective patient supports 235, 236 are completely independent. Thus, the upper patient on support 235 is shown positioned for what could be a head scan or a scan of the cervical spine. The lower patient on support 236 is positioned for what could be an abdominal scan, or a scan of the lumbar spine. Thus, multiple patients can be in the magnet gap simultaneously and scanned at the same time without limitation as to what part of the anatomy of the different patients is available for simultaneous MR imaging or other MR study.

Multi-patient scanning which is enabled by the expanded access of the open entry magnets and the larger gap sizes of the invention is important for reducing the cost of magnetic resonance scans. Simultaneous scanning increases the number of patients per hour that can be studied, i.e. thruput, and improves the utilization of expensive magnetic resonance systems, thereby resulting in lower unit cost per scan.

The open entry features of the magnet disclosed herein allow for the possibility of new medical techniques being carried out in cooperation with magnetic resonance scanning. In particular, magnetic resonance guided surgery is possible through the use of open entry magnets. The use of magnetic resonance during the surgical procedure is particularly fostered by two attributes of magnetic resonance. First, the level of image detail of soft tissue body parts is exceptional and unprecedented by prior technologies such as x-ray, CAT scan, ultrasound, nuclear medicine, etc. and provides a new level of anatomic detail to guide the surgical procedure during surgery and a new means for fine detail visualization during surgery to guide the surgeon. Additionally, MR permits the surgeon to operate while the MR scan is on where he could not safely do so within the hazardous x-ray fields of the CAT scanner, nuclear medicine scanner or other x-ray visualizing techniques. The use of magnetically tipped probes or other MR visible surgical instruments will allow the surgeon the ability to position his instruments by MR visualization.

Magnetic resonance guided surgery is carried out by providing a magnet having open entry construction. The patient is disposed within the magnet gap, and at least one magnetic resonance image of the anatomy of the region of the patient upon which surgery is to be performed is acquired. The surgery is commenced and additional magnetic resonance images of the anatomy of the region of the patient undergoing surgery are acquired during the course of the surgery. These additional magnetic resonance images show the effects of the surgery during its course. The additional MR images are used for guiding the course of the surgery so that anatomical changes, and other effects of the surgery, can be viewed by the surgeon without having to visually observe the region of the patient where the surgery is being carried out.

This surgery is advantageously carried out while the patient remains within the magnet. This allows for the continuous monitoring of the surgery by MR imaging throughout the entire course of the surgery.

With respect to magnetic resonance guided surgery it would be advantageous both for optimum MR visualization and MR guided surgical procedures to position the patient through the utilization of a scanning bed that can position the patients anterior-posterior axis at an angle that is arbitrary with respect to the main magnetic field, i.e. not necessarily zero or 900. Such positioning capability available through an obliquing bed that can take advantage of the larger gap size of open entry magnets will allow a surface coil to be applied to the patient's anatomy to be positioned for the optimum anatomic position without restriction on the placement of the coil relative to the magnetic field for optimum sensitivity. Maximum MR sensitivity can then be achieved by rotation of the patient to an arbitrary angle to maximize MR sensitivity.

In analogous fashion a scanning bed that can likewise position that patient in the magnetic field so that either his lateral axis or longitudinal axis forms an arbitrary non-zero and non-orthogonal angle with respect to the magnet will exploit the larger gap size of the open entry magnet design for optimum MR sensitivity, optimum positioning for MR guided surgery and optimum anatomic positioning of MR surface coils.

It would be advantageous for a number of MR applications both in MR imaging and MR guided surgery to have available a single apparatus that would allow MR scanning at two orientations of the magnetic field (e.g. magnetic field horizontally oriented, magnetic field vertically oriented). Such a magnet would enable a fuller range of MR applications in MR imaging and MR guided surgery than are currently possible. In particular, a magnetic apparatus with a pole pair (FIGS. 14B and 14C) that could be rotated prior to any procedure for its most advantageous magnetic field orientation with respect to the body part being examined would provide optimum medical cost-effectiveness and optimum MR diagnosis and MR guided therapy.

As described herein, the magnets according to the invention have a patient-receiving gap and are suitable for carrying out medical magnetic resonance studies. The magnets are described being used to conduct specific medical procedures which entail magnetic resonance studies of a patient. However, these magnets have other applications such as non-destructive testing of industrial sized articles. Accordingly, the magnets and facilities claimed herein are not limited to magnets and facilities which are intended only for medical applications, and the scope of the claims should be read without imputing any limitations to medical applications unless such a limitation is expressly recited.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Magnetic resonance imaging apparatus having a variable field direction comprising:

a pair of opposed ferromagnetic pole surfaces disposed facing each other and defining therebetween a patient-receiving gap for receiving a patient to be studied by magnetic resonance and a polar axis extending between said pole surfaces through said gap;

a yoke comprised of ferromagnetic material for providing a magnetic flux return circuit for magnetic flux which passes from one pole surface to the other through the patient-receiving gap;

a magnet for generating magnetic flux flowing from one to the other of said pole surfaces through the patient-receiving gap; and a support for mounting said pole surfaces on said yoke for movement of said pole surfaces with respect to said yoke so that said pole axis can be tilted to an arbitrary angle with respect to the vertical.

2. Apparatus according to claim 1, wherein said yoke is generally ring-shaped and extends around a ring center, the magnet further including a pair of poles extending inwardly from said ring-shaped yoke towards said ring center each said pole having one of said pole surfaces;

said support being effective for mounting said yoke with the plane of said yoke vertical and for mounting said poles for movement along said yoke to thereby rotate said polar axis about the ring center; and said magnet is effective for generating magnetic flux in opposite directions within said ring-shaped yoke for forcing magnetic flux through said poles and across the patient-receiving gap.

3. Magnetic resonance imaging apparatus having a variable field direction comprising:

a pair of opposed ferromagnetic pole surfaces disposed facing each other and defining therebetween a patient-receiving gap for receiving a patient to be studied by magnetic resonance;

a yoke comprised of ferromagnetic material for providing a magnetic flux return circuit for magnetic flux which passes from one pole surface to the other through the patient-receiving gap;

a magnet for generating magnetic flux flowing from one to the other of said pole surfaces through the patient-receiving gap;

wherein said yoke is a polygon approximation of a circular ring of at least five sides.

4. Apparatus according to claim 3, further comprising a pair of ferromagnetic poles each having a pole face with the patient-receiving gap between the pole faces of said pair of poles;

wherein said support is effective for mounting said yoke with the plane of said yoke vertical; and said means for generating magnetic flux is effective for generating magnetic flux in opposite directions within said ring-shaped yoke for forcing magnetic flux through said poles and across the patient-receiving gap.

* * * * *